US012758581B2

(12) United States Patent
Castro et al.

(10) Patent No.: US 12,758,581 B2
(45) Date of Patent: Oct. 13, 2026

(54) USE OF PLASMA AND PLASMA FRACTIONS FOR IMPROVEMENT OF PAIN, WOUND HEALING, AND POSTOPERATIVE RECOVERY

(71) Applicant: Alkahest, Inc., San Carlos, CA (US)

(72) Inventors: Marian Castro, Redwood City, CA (US); Ian Gallager, Half Moon Bay, CA (US); Viktoria Kheifets, Mountain View, CA (US)

(73) Assignee: Alkahest, Inc., San Carlos, CA (US)

( * ) Notice: Subject to any disclaimer, the term of this patent is extended or adjusted under 35 U.S.C. 154(b) by 489 days.

(21) Appl. No.: 18/199,652

(22) Filed: May 19, 2023

(65) Prior Publication Data

US 2023/0285455 A1 Sep. 14, 2023

Related U.S. Application Data

(60) Continuation of application No. 18/075,805, filed on Dec. 6, 2022, which is a continuation of application No. 17/115,144, filed on Dec. 8, 2020, now Pat. No. 11,547,724, which is a division of application No. 16/659,000, filed on Oct. 21, 2019, now Pat. No. 11,103,530.

(60) Provisional application No. 62/842,403, filed on May 2, 2019, provisional application No. 62/751,448, filed on Oct. 26, 2018.

(51) Int. Cl.

| | |
|---|---|
| ***A61K 35/16*** | (2015.01) |
| ***A61K 9/00*** | (2006.01) |
| ***A61K 38/38*** | (2006.01) |
| ***A61P 29/00*** | (2006.01) |

(52) U.S. Cl.

CPC ............ *A61K 35/16* (2013.01); *A61K 9/0014* (2013.01); *A61K 38/38* (2013.01); *A61P 29/00* (2018.01)

(58) Field of Classification Search

None

See application file for complete search history.

(56) References Cited

U.S. PATENT DOCUMENTS

| | | | |
|---|---|---|---|
| 4,075,197 A | 2/1978 | Schuck et al. | |
| 4,391,801 A | 7/1983 | Ng et al. | |
| 4,624,768 A | 11/1986 | Yoshida et al. | |
| 4,900,720 A | 2/1990 | Kotitschke | |
| 5,138,034 A | 8/1992 | Uemura et al. | |
| 5,792,835 A | 8/1998 | Tse et al. | |
| 5,916,202 A | 6/1999 | Haswell | |
| 6,632,174 B1 | 10/2003 | Breznitz | |
| 6,946,546 B2 | 9/2005 | Vaughan et al. | |
| 7,785,601 B2 | 8/2010 | Schaebitz et al. | |
| 7,851,446 B2 | 12/2010 | Roura | |
| 10,245,285 B2 | 4/2019 | Braithwaite et al. | |
| 10,357,513 B2 | 7/2019 | Braithwaite et al. | |
| 10,525,107 B2 | 1/2020 | Bell et al. | |
| 10,905,717 B2 | 2/2021 | Braithwaite et al. | |
| 11,040,068 B2 | 6/2021 | Braithwaite et al. | |
| 11,103,530 B2 * | 8/2021 | Castro | A61K 38/38 |
| 11,547,724 B2 * | 1/2023 | Castro | A61P 29/00 |
| 2002/0143283 A1 | 10/2002 | Braverman et al. | |
| 2002/0151064 A1 | 10/2002 | Rothenberg et al. | |
| 2003/0157687 A1 | 8/2003 | Greene et al. | |
| 2003/0194397 A1 | 10/2003 | Mishra | |
| 2004/0120937 A1 | 6/2004 | Wilson | |
| 2004/0127445 A1 | 7/2004 | Liew et al. | |
| 2004/0141946 A1 | 7/2004 | Schaebitz et al. | |
| 2004/0146565 A1 | 7/2004 | Strohbehn et al. | |
| 2004/0254152 A1 | 12/2004 | Monje et al. | |
| 2005/0142208 A1 | 6/2005 | Yoo et al. | |
| 2005/0221348 A1 | 10/2005 | Ray et al. | |
| 2006/0094064 A1 | 5/2006 | Ray et al. | |
| 2006/0198851 A1 | 9/2006 | Basi et al. | |
| 2006/0263759 A1 | 11/2006 | Alves-Filho et al. | |
| 2007/0010435 A1 | 1/2007 | Frangione et al. | |
| 2007/0037200 A1 | 2/2007 | Ray et al. | |
| 2007/0117180 A1 | 5/2007 | Morikawa et al. | |
| 2007/0155725 A1 | 7/2007 | Li et al. | |
| 2007/0190055 A1 | 8/2007 | Ambati | |
| 2008/0026485 A1 | 1/2008 | Hueber et al. | |
| 2008/0057590 A1 | 3/2008 | Urdea et al. | |
| 2008/0287354 A1 | 11/2008 | O'Brien et al. | |
| 2009/0111740 A1 | 4/2009 | Grifols Roura | |
| 2009/0143394 A1 | 6/2009 | Wyss-Coray et al. | |
| 2009/0181008 A1 | 7/2009 | Ray et al. | |
| 2009/0239241 A1 | 9/2009 | Ray et al. | |

(Continued)

FOREIGN PATENT DOCUMENTS

| | | |
|---|---|---|
| AU | 684202 A | 2/1996 |
| CA | 2641830 A1 | 4/2009 |

(Continued)

OTHER PUBLICATIONS

Adair et al., "Measurement of gelatinase B (MMP-9) in the cerebrospinal fluid of patients with vascular dementia and Alzheimer disease." Stroke. Jun. 2004;35(6):e159-62.

Adkins et al., "Toward a Human Blood Serum Proteome", (2002) Molecular & Cellular Proteomics 1: 947-955.

Anderson et al., "The Human Plasma Proteome", (2002) Molecular & Cellular Proteomics 1: 845-867.

Anderson et al., "High resolution two-dimensional electrophoresis of human plasma proteins", (1977) Proc. Natl. Acad. Sci. vol. 74, No. 12, pp. 5421-5425.

Baba et al., "Timp-3 deficiency impairs cognitive function in mice." Lab Invest. Dec. 2009;89(12):1340-7.

(Continued)

*Primary Examiner* — Russell G Fiebig

(74) *Attorney, Agent, or Firm* — Mandar A. Joshi; Bret E Field; Bozicevic, Field & Francis LLP

(57) ABSTRACT

Methods and compositions for improving postoperative recovery are described. The compositions used in the methods include blood plasma and blood plasma fractions derived from blood plasma with efficacy in treating and/or preventing conditions associated with postoperative recovery.

20 Claims, 28 Drawing Sheets

(56) References Cited

U.S. PATENT DOCUMENTS

Figure 1:
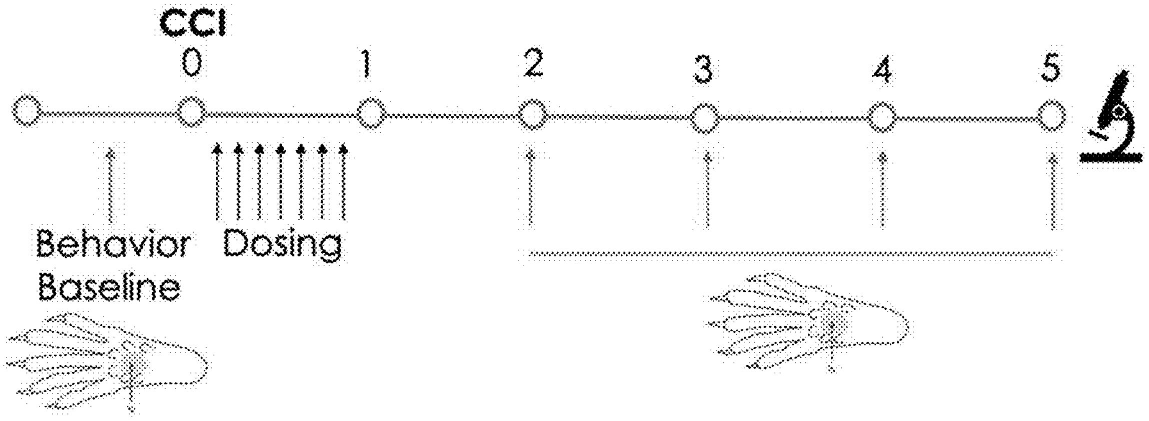

| | | | |
|---|---|---|---|
| 2010/0080850 | A1 | 4/2010 | Hubbel et al. |
| 2010/0124756 | A1 | 5/2010 | Ray et al. |
| 2010/0258496 | A1 | 10/2010 | Hidaka et al. |
| 2010/0310609 | A1 | 12/2010 | Watson et al. |
| 2010/0324079 | A1 | 12/2010 | Ohyagi |
| 2011/0117100 | A1 | 5/2011 | Britschgi et al. |
| 2011/0202284 | A1 | 8/2011 | McReynolds et al. |
| 2011/0212854 | A1 | 9/2011 | Ray et al. |
| 2011/0243947 | A1 | 10/2011 | Doody et al. |
| 2012/0095000 | A1 | 4/2012 | Wyss-Coray et al. |
| 2012/0258075 | A1 | 10/2012 | Wyss-Coray et al. |
| 2013/0040844 | A1 | 2/2013 | Wyss-Coray et al. |
| 2013/0102537 | A1 | 4/2013 | Bairstow et al. |
| 2013/0121979 | A1 | 5/2013 | Mishra |
| 2013/0302322 | A1 | 11/2013 | Wong et al. |
| 2014/0011689 | A1 | 1/2014 | Sandip et al. |
| 2014/0121438 | A1 | 5/2014 | Long et al. |
| 2014/0255424 | A1 | 9/2014 | Wyss-Coray et al. |
| 2014/0271669 | A1 | 9/2014 | Hofbauer et al. |
| 2014/0328856 | A1 | 11/2014 | Gelmont et al. |
| 2015/0064164 | A1 | 3/2015 | Edwards et al. |
| 2015/0079045 | A1 | 3/2015 | Kong |
| 2015/0157664 | A1 | 6/2015 | Wyss-Coray et al. |
| 2016/0143996 | A1 | 5/2016 | Wyss-Coray et al. |
| 2016/0208011 | A1 | 7/2016 | Wyss-Coray et al. |
| 2017/0081415 | A1 | 3/2017 | Wong et al. |
| 2017/0232118 | A1 | 8/2017 | Wyss-Coray et al. |
| 2018/0110839 | A1 | 4/2018 | Bell et al. |
| 2019/0321449 | A1 | 10/2019 | Bell et al. |
| 2020/0129550 | A1 | 4/2020 | Castro et al. |
| 2022/0152161 | A1 | 5/2022 | Bell et al. |

FOREIGN PATENT DOCUMENTS

| | | | |
|---|---|---|---|
| CA | 2641830 | C | 7/2013 |
| CN | 201453773 | U | 5/2010 |
| CN | 113164508 | A | 7/2021 |
| CN | 114867488 | A | 8/2022 |
| EP | 0091784 | A2 | 10/1983 |
| EP | 0184040 | B1 | 4/1993 |
| EP | 19930184040 | B1 | 4/1993 |
| EP | 1393740 | A1 | 3/2004 |
| EP | 2111868 | B1 | 8/2013 |
| EP | 3484502 | B1 | 8/2021 |
| JP | 2013-173767 | A | 9/2013 |
| KR | 10-0782333 | B1 | 12/2007 |
| RU | 2197991 | C1 | 2/2003 |
| RU | 2428997 | C1 | 9/2011 |
| RU | 2429013 | C2 | 9/2011 |
| RU | 2466141 | C2 | 11/2012 |
| RU | 2470677 | C1 | 12/2012 |
| SU | 1212416 | A1 | 2/1986 |
| UA | 35656 | C2 | 4/2001 |
| WO | WO0191713 | A1 | 12/2001 |
| WO | WO03007874 | A1 | 1/2003 |
| WO | WO2005052592 | A2 | 6/2005 |
| WO | WO2005106492 | A2 | 11/2005 |
| WO | WO2006084334 | A1 | 8/2006 |
| WO | WO2006133423 | A1 | 12/2006 |
| WO | WO2007059135 | A2 | 5/2007 |
| WO | WO2007139291 | A1 | 12/2007 |
| WO | WO2009023814 | A2 | 2/2009 |
| WO | WO2009055729 | A1 | 4/2009 |
| WO | WO2009155069 | A1 | 12/2009 |
| WO | WO2011028733 | A1 | 3/2011 |
| WO | WO2011094535 | A2 | 8/2011 |
| WO | WO2013142135 | A1 | 9/2013 |
| WO | WO2015088915 | A1 | 6/2015 |
| WO | WO2016187217 | A2 | 11/2016 |
| WO | WO2016205004 | A2 | 12/2016 |
| WO | WO2017025965 | A1 | 2/2017 |
| WO | WO2017120461 | A1 | 7/2017 |
| WO | WO2020086469 | A1 | 4/2020 |

OTHER PUBLICATIONS

Berezovskaya et al., “Colony stimulating factor-1 potentiates neuronal survival in cerebral cortex ischemic lesion.” Acta Neuropathol. Nov. 1996;92(5):479-86.

Boissonneault et al., “Powerful beneficial effects of macrophage colony-stimulating factor on beta-amyloid deposition and cognitive impairment in Alzheimer’s disease.” Brain. Apr. 2009;132(Pt 4):1078-92.

Bouchard et al., “Aging and brain rejuvenation as systemic events,” J. Neurochem. Jan. 2015; 132(1):5-19.

Britschgi et al., “Blood protein signature for the early diagnosis of Alzheimer disease.” Arch Neurol. Feb. 2009;66(2):161-5.

Cheung et al., “Serum β-2 microglobulin predicts mortality in people with diabetes.” Eur J Endocrinol. May 17, 2013;169(1):1-7.

Fedoroff et al., “Role of colony stimulating factor-1 in brain damage caused by ischemia.” Neurosci Biobehav Rev. Mar. 1997;21(2):187-91.

Gowing et al., “Macrophage colony stimulating factor (M-CSF) exacerbates ALS disease in a mouse model through altered responses of microglia expressing mutant superoxide dismutase.” Exp Neurol. Dec. 2009;220(2):267-75.

Jha, “Young blood can reverse some effects of ageing, study finds,” The Guardian, Oct. 17, 2012, 4 pages.

Kwak et al., “Aging, exercise, and extracellular matrix in the heart.” J Exerc Rehabil. Jun. 30, 2013;9(3):338-47.

Lin et al., “Discovery of a cytokine and its receptor by functional screening of the extracellular proteome.” Science. May 9, 2008;320(5877):807-11.

Luo et al., “Colony-stimulating factor 1 receptor (CSF1R) signaling in injured neurons facilitates protection and survival.” J. Exp. Med. (2013) 210(1):157-172.

Lysaght et al., “Beta-2 microglobulin removal during continuous ambulatory peritoneal dialysis (CAPD).” Perit Dial Int. 1989;9(1):29-35.

Malkki, “Ageing: Could young blood combat age-related cognitive decline?” Nat. Rev. Neurol. Jun. 2014;10(6):307.

Manzo et al., “Role of chemokines and chemokine receptors in regulating specific leukocyte trafficking in the immune/inflammatory response.” Clin Exp Rheumatol. Jul.-Aug. 2003;21(4):501-8.

Mclaurin et al., “Microglial pilgrimage to the brain.” Nat Med. Dec. 2010;16(12):1380-1.

Middeldorp et al., “A young systemic environment reverses degeneration in a mouse model of Alzheimer’s disease,” Neuroscience 2012, Presentation Abstract, Oct. 16, 2012, 2 pages.

Mitrasinovic et al., “Microglia overexpressing the macrophage colony-stimulating factor receptor are neuroprotective in a microglial-hippocampal organotypic coculture system.” J Neurosci. Apr. 27, 2005;25(17):4442-51.

Mizuno et al., “Interleukin-34 selectively enhances the neuroprotective effects of microglia to attenuate oligomeric amyloid-β neurotoxicity.” Am J Pathol. Oct. 2011;179(4):2016-27.

Palop et al., “A network dysfunction perspective on neurodegenerative diseases.” Nature. Oct. 19, 2006;443(7113):768-73.

Prakasam et al., “Amyloid and neurodegeneration: Alzheimer’s disease and retinal degeneration.” Chapter 7, Handbook of Neurochemistry and Molecular Neurobiology, Lajtha ed., 2009, 131-163. (Year: 2009).

Ron-Harel et al., “Age-Dependent Spatial Memory Loss Can Be Partially Restored by Immune Activation,” Rejuvenation Resarch (2008), 11(5):903-13.

Royer et al., “A novel antagonist of prostaglandin 02 blocks the locomotion of eosinophils and basophils.” Eur J Clin nvesl. Sep. 2008;38(9):663-71.

Schwartz et al., “How Do Immune Cells Support and Shape the Brain in Health, Disease, and Aging?” The Journal of Neuroscience, Nov. 6, 2013, 33(45):17587-96.

Sellebjerg et al., “Identification of new sensitive biomarkers for the in vivo response to interferon-beta treatment in multiple sclerosis using DNA-array evaluation.” Eur J Neurol. Dec. 2009;16(12):1291-8.

Shin et al., “Association of eotaxin gene family with asthma and serum total IgE.” Hum Mol Genet. Jun. 1, 2003;12(11):1279-85.

(56) References Cited

OTHER PUBLICATIONS

Skovronsky et al., "Neurodegenerative diseases: new concepts of pathogenesis and their therapeutic implications." Annu Rev Pathol. 2006;1:151-70.
Smith et al., "β2-microglobulin is a systemic pro-aging factor that impairs cognitive function and neurogenesis." Nat Med. Aug. 2015;21(8):932-7.
Strobel et al., "Chicago: the vampire principle—young blood rejuvenates aging brain?" Alzheimer Research Forum (Nov. 2009), p. 1-3.
Stubbs et al., "Indomethacin causes prostaglandin 0(2)-like and eotaxin-like selective responses in eosinophils and basophils." J Biol Chem. Jul. 19, 2002;277(29):26012-20.
Teixeira et al., "Increased serum levels of CCL 11/eotaxin in schizophrenia," "Process in neuro-psychopharmacology & biological psychiatry," vol. 32, No. 3, pp. 710-714, 2008.
Thomson et al., "Young blood for a keener mind," New Scientist (2012), 216(2887): 10.
Villeda et al., "Changes in the systemic milieu modulate neurogenesis during aging." Abstract, 39th Annual Neuroscience Meeting, Chicago, IL, Society for Neuroscience, Oct. 2009, 1-2. (Year: 2009).
Villeda et al., "The aging systemic milieu negatively regulates neurogenesis and cognitive function," Nature, Aug. 31, 2011, 477(7362):90-4.
Villeda et al., "Young blood reverses age-related cognitive impairments," Neuroscience 2012, Presentation Abstract, Oct. 17, 2012, 2 pages.
Villeda et al., "Young blood reverses age-related impairments in cognitive function and synaptic plasticity in mice," Nat Med. (Jun. 2014), 20(6):659-63.
Vincent et al., "Macrophage colony stimulating factor prevents NMDA-induced neuronal death in hippocampal organotypic cultures." J Neurochem. Sep. 2002;82(6):1388-97.
Wang et al., "Expression of colony stimulating factor-1 receptor (CSF-1R) by CNS neurons in mice." J Neurosci Res. Sep. 1, 1999;57(5):616-32.
Wang et al., "Matrix metalloproteinases and their multiple roles in Alzheimer's disease." Biomed Res Int. 2014;2014:908636.
Wilson et al., "Beta2-microglobulin as a biomarker in peripheral arterial disease: proteomic profiling and clinical studies." Circulation. Sep. 18, 2007;116(12):1396-403.
Yagihashi et al., "Macrophage colony stimulating factor (M-CSF) protects spiral ganglion neurons following auditory nerve injury: morphological and functional evidence." Exp Neurol. Mar. 2005;192(1):167-77.
Yamane et al., "CSF-1 receptor-mediated differentiation of a new type of monocytic cell with B cell-stimulating activity: its selective dependence on IL-34." J Leukoc Biol. Jan. 2014;95(1):19-31.
Ye et al., "Haptoglobin-alpha subunit as potential serum biomarker in ovarian cancer: identification and characterization using proteomic profiling and mass spectrometry." Clinical Cancer Research (Aug. 2003), 9(8):2904-11.
Bhattacharya, "Placental umbilical cord whole blood transfusion. A safe and genuine blood substitute for patients of the under-resourced areas of this country at emergency." J Am Coll Surg. 2005. Submitted 34 pages.
Bhattacharya, "Study of the utility of placental cord blood in meeting the transfusion needs of beta-thalassaemic patients." Regional Health Forum, 2008. pp. 16-27.
Borlongan et al., "Central Nervous System Entry of Peripherally Injected Umbilical Cord Blood Cells is Not Required for Neuroprotection in Stroke." Stroke. 2004. pp. 2385-2389. Dallas, Texas.
Conboy et al., "Heterochronic parabiosis for the study of the effects of aging on stem cells and their niches." Cell Cycle. 2012. pp. 2260-2268.
Conboy et al., "Heterochronic parabiosis: Historical perspective and methodological considerations for studies of aging and longevity," Aging Cell, available online Apr. 2013. pp. 525-530.
Conboy et al., "Rejuvination of aged progenitor cells by exposure to a young systemic environment." Nature. 2005. pp. 760-764.
Katcher, "Studies that Shed New Light on Aging." Biochemistry (Moscow), Sep. 2013. pp. 1061-1070.
Loffredo et al., "Growth Differentiation Factor 11 is a Circulating Factor that Reverses Age-Related Cardiac Hypertrophy." Cell. May 2013. pp. 828-839.
Krementsov, "A Martian Stranded on Earth: Alexander Bogdanov, Blood Transfusions, and Proletarian Science." pp. 57-59, 85, 86, and 88. University of Chicago Press, Chicago, United States, 2011.
Boada et al., "Treatment of Alzheimer disease using combination therapy with plasma exchange and haemapheresis with albumin and intravenous immunoglobulin: Rationale and treatment approach of the AMBAR (Alzheimer Management by Albumin Replacement) study." Neurologia, vol. 31, No. 7, pp. 473-481 (Jul. 29, 2016). See abstract; p. 479.
Hughes et al., "Clinical applications of intravenous immunoglobulins in neurology." Clinical and Experimental Immunology, vol. 158, supple.1, pp. 34-42 (2009). See abstract; pp. 38-40.
Website document entitled "Plasma Protein Composition" (available at http://www.sigmaaldrich.com/life-science/metabolomics/enzyme-explorer/learning-center/plasma-blood-proteins/plasma-protein-composition.html). Downloaded on Jun. 27, 2017.
"Young blood can reverse some effects of ageing, study finds," Society for Neuroscience, The Observer, Oct. 24, 2012, 2 pages, Retrieved online: http://gonzoj.wordpress.com/tag/society-for-neuroscience/.
Albumin (Human) U.S.P. 2012 (Year: 2012).
Plasma protein fraction (human), Bayer 2002, pp. 1-5 (Year: 2002).
Chapter I—Food and Drug Administration, Department of Health and Human Services, FDA 21, CFR 640.92.2001. (Year: 2001), 2 pages.
Conboy et al., Heterochronic parabiosis for the study of the effects of aging on stem cells and their niches, Cell Cycle, 2012, vol. 11, No. 12, p. 2260-2267.
Crisp et al., The effects of aging on thermal hyperalgesia and tactile-evoked allodynia using two models of peripheral mononeuropathy in the rat, Neuroscience Letters, 2003, vol. 339, p. 103-106.
Pietramaggiori et al., Improved Cutaneous Healing in Diabetic Mice Exposed to Healthy Peripheral Circulation, Journal of Investigative Dermatology, 2009, vol. 129, p. 2265-2274.
Ruckh et al., Rejuvenation of regeneration in the aging central nervous system, Cell Stem Cell, 2012, vol. 10, No. 1, p. 96-103.
Song et al., Use of the Parabiotic Model in Studies of Cutaneous Wound Healing to Define Participation of Circulating Cells, Wound Repair Regen, 2010, vol. 18, No. 4, p. 426-432.
Taniguchi et al., Intra-articular platelet-rich plasma (PRP) injections for treating knee pain associated with osteoarthritis of the knee in the Japanese population: a phase I and IIa clinical trial, Nagoya J Med Sci. Feb. 2018;80(1):39-51.
Munsch et al., Hydroxyethyl starch: an alternative to plasma for postoperative volume expansion after cardiac surgery, BJS Society, vol. 75, Issue7, Jul. 1988, pp. 675-678.
Cai et al., Is albumin administration beneficial in early stage of postoperative hypoalbuminemia after gastrointestinal surgery: a prospective randomized control trial, Zhonghua Wai Ke Za Zhi. May 15, 2009;47(10):744-7.
Lacci et al., Review—Platelet-Rich Plasma: Support for Its Use in Wound Healing, Yale Journal of Biology and Medicine, 83 (2010), pp. 1-9.
Flury et al., Does Pure Platelet-Rich Plasma Affect Postoperative Clinical Outcomes After Arthroscopic Rotator Cuff Repair? A Randomized Controlled Trial, Am J Sports Med. Aug. 2016;44(8):2136-46.
Matejtschuk et al., Production of human albumin solution: a continually developing colloid, British Journal of Anaesthesia, 85(6):887-95, Dec. 2000.
Plasmanate, Plasma Protein Fraction (Human) 5%, USP, 14-7613-008, Apr. 1998, http://www.ctint.org/inserts/Plasmanate5_insert.pdf.
Winkler et al., Chapter 33, Albumin and Related Products, Transfusion Medicine and Hemostasis, Academic Press, pp. 185-191 (2009).
Hong et al., Aging-associated sensory decline and Alzheimer's disease, Mol Neurodegener, 19(1):93 (Dec. 4, 2024).

(56) References Cited

OTHER PUBLICATIONS

Al-Temaimi et al., Remyelination modulators in multiple sclerosis patients, Experimental and Molecular Pathology, 103(3):237-241, 2017.
Dodel et al, "Human antibodies against amyloid β peptide: A potential treatment for Alzheimer's disease", Ann Neurol, vol. 52, Issue 2, pp. 253-256, Aug. 2022.
Hink et al., Preparation and properties of a heat-treated human plasma protein fraction, Vox Sang, Jul. 1957; 2(3):174-86.
Kelliher, IVIg therapy may improve cognitive function in alzheimer's patients, Cornell Chronicle, Apr. 13, 2005, https://news.cornell.edu/stories/2005/04/ivig-therapy-may-improve-cognitive-function-alzheimers-patients, accessed Nov. 21, 2022, 5 pages.
Kile et al., IVIG treatment of mild cognitive impairment due to Alzheimer's disease: a randomised double-blinded exploratory study of the effect on brain atrophy, cognition and conversion to dementia, J Neurol Neurosurg Psychiatry, Feb. 2017; 88(2):106-112; Abstract Only.
NHS, Treatment of Alzheimer's disease, https://www.nhs.uk/conditions/alzheimers-disease/treatment/; Page last reviewed: Jul. 5, 2021 (Year: 2021), printed on Jun. 15, 2023, 2 pages.
Sapir et al., Uncovering the Hidden Potential of Intravenous Immunoglobulin as an Anticancer Therapy, Clin Rev Allergy Immunol, Dec. 2005; 29(3):307-10.
USP Monographs: Plasma Protein Fraction, U.S. Pharmacopeia, www.pharmacopeia.cn/v29240/sp29nf24s0_m65900.html, accessed on Mar. 8, 2022, 1 page.
Volkov, Technology of immunoglobulin production, Technological aspects of purification, Ukrainian journal of biochimestry, 2006, vol. 78, No. 3, pp. 88-98; English summary enclosed on p. 96-97.
Brazier, Medical News Today, https://www.medicalnewstoday.com/articles/323396[May 27, 2021 12:44:57 PM] (Year: 2021).
Yuan et al., Is albumin administration beneficial in early stage of postoperative hypoalbuminemia after gastrointestinal surgery: a prospective randomized control trial, Randomized Controlled Trial Am J Surg, Nov. 2008; 196(5):751-5.
Cocciolo et al., Decreased expression and increased oxidation of plasma haptoglobin in Alzheimer disease: Insights from redox proteomics, Free Radic Biol Med, Nov. 15, 2012; 53(10):1868-76.
Kosheleva et al., Plasma Therapy: Methods and Areas of Application, Attending physician, No. 01, 2018, p. 59-66.
Dyke et al., Plasma exchange in chronic inflammatory demyelinating polyradiculoneuropathy, N Engl J Med. Feb. 20, 1986;314(8):461-5.
Harsan et al., Brain dysmyelination and recovery assessment by noninvasive in vivo diffusion tensor magnetic resonance imaging, J Neurosci Res. Feb. 15, 2006;83(3):392-402.
Keegan et al., Relation between humoral pathological changes in multiple sclerosis and response to therapeutic plasma exchange, Lancet. Aug. 2005;366(9485):579-82.
Purves et al., ncreased Conduction Velocity as a Result of Myelination, Neuroscience, 2nd edition, 2001.
Reich et al., Multiple Sclerosis, N Engl J Med. Jan. 11, 2018;378(2):169-180.
Yan et al., Passive transfer of demyelination by serum or IgG from chronic inflammatory demyelinating polyneuropathy patients, Ann Neurol. Jun. 2000;47(6):765-75.
Horiuchi et al., Amyloid β1-42 oligomer inhibits myelin sheet formation in vitro, Neurobiol Aging. Mar. 2012;33(3):499-509.
Lee et al., Gabapentin inhibits the analgesic effects and nerve regeneration process induced by hepatocyte growth factor (HGF) in a peripheral nerve injury model: Implication for the use of VM202 and gabapentinoids for peripheral neuropathy, Mol Cell Neurosci. Sep. 2022:122:103767.
Rose et al., Gabapentin: pharmacology and its use in pain management, Anaesthesia. May 2002;57(5):451-62.
Solomon, Multifunctional effect of human serum albumin reduces alzheimer disease related pathologies in the 3XTG mice model. Abstracts / Neurobiology of Aging 39 (2016) S1-S13. (Year: 2016).

* cited by examiner

Diabetic Wound - No Treatment

Diabetic Wound - PPF1 Treated

Diabetic Wound - No Treatment

Diabetic Wound - PPF1 Treated

USE OF PLASMA AND PLASMA FRACTIONS FOR IMPROVEMENT OF PAIN, WOUND HEALING, AND POSTOPERATIVE RECOVERY

I. CROSS REFERENCE TO RELATED APPLICATIONS

This application is a continuation of U.S. patent application Ser. No. 18/075,805 filed Dec. 6, 2022, which application is a continuation of U.S. patent application Ser. No. 17/115,144 filed Dec. 8, 2020, now issued as U.S. Pat. No. 11,547,724, which application is a division of U.S. patent application Ser. No. 16/659,000 filed Oct. 21, 2019, now issued as U.S. Pat. No. 11,103,530, which application, pursuant to 35 U.S.C. § 119 (e), claims priority to the filing dates of U.S. Provisional Patent Application No. 62/751,448 filed Oct. 26, 2018 and U.S. Provisional Patent Application No. 62/842,403 filed May 2, 2019; the disclosures of which applications are herein incorporated by reference.

II. FIELD

This invention pertains to the prevention and treatment of disease and aging-associated disease. The invention relates to the use of blood products, such as blood plasma and blood plasma fractions to improve and accelerate recovery from surgery, including conditions and indications related to surgery. The invention also relates to the use of blood products, such as blood plasma and blood plasma fractions to alleviate chronic pain or neuropathy and to treat indications related to wound healing.

III. BACKGROUND

The following is offered as background information only and is not admitted as prior art to the present invention.

Surgery is often associated with complications from pain, cardiopulmonary issues, infections, thromboembolic issues, and postsurgical wound healing. Additionally, it takes time for wounds to heal whether incurred from surgery itself (e.g. incisions) or incurred by accident, force, or disease and subsequently treated by a surgical procedure. Such complications are often further exacerbated by age. Additional complications may arise from the surgical stress response with subsequent demand on organ function, which are often mediated by trauma-induced endocrine metabolic changes and activation of cascades (cytokines, complement, arachidonic acid metabolites, nitric oxide, and free oxygen radicals). (Kehlet H., et al., *Br. J. Anaesthesia,* 78:606-17 (1997)). During surgical stress response, the sympathetic nervous system is activated. (Starkweather A, et al., Topics in Pain Management, 32(8):1-11 (2017)). There is an increase in pituitary hormone secretion, resulting in mobilization of energy through catabolism. This in turn results in salt and water retention. Adrenocorticotropic hormone (ACTH) secretion is increased, which results in an increase of norepinephrine and sympathetic activity. This causes cardiovascular responses such as tachycardia and hypertension and glucagon is released resulting in hyperglycemia. An increase in growth hormone and cortisol also results in inhibition of monocyte to macrophage differentiation. This in turn, interferes with T-cell signaling/histamine production and decreases immune cell migration. (Id.)

Current treatment for postsurgical recovery includes reduction of postoperative pain as well as multimodal interventions. (Id.) Pain management is important in many types of surgical recoveries, and acute pain is expected. (Pinto P R, *J Pain Res,* 10:1087-98 (2017)). Postoperative pain is associated to a greater degree with patients who undergo general surgery. (Couceiro T C, *Rev Bras Anestesiol,* 59(3): 314-20 (2009)). Pain also plays a negative role on clinical outcome because it impairs healing and recovery. Id. Replacement of the hip and knee joints is particularly associated with pain, both chronic (from, e.g. osteoarthritis) and acute. Id. Analgesics are therefore commonly used in postoperative recovery, both during in-patient procedures and home recovery.

One type of multimodal intervention is Enhanced Recovery After Surgery (ERAS). (Starkweather A, supra). ERAS focuses on a wide spectrum of surgeries, for example, colorectal surgery, orthopedics, gynecology, urology, head and neck cancer, bladder cancer, liver disease, rectal/pelvic disease, colonic pathologies, pancreative duodenectomy, gastrectomy, and bariatric and gynecologic-oncology surgery. Id. As a multimodal strategy, it emphasizes: preoperative techniques (counseling, fluid/carbohydrate loading; shorter period of fasting); perioperative techniques (short-acting anesthetics; normothermia; antibiotic prophylaxis; thromboembolic prophylaxis; prevention of salt/water overload; vomiting prevention); and postoperative techniques (early oral diet; exercise; non-opioid analgesia; and post-discharge support). Id.

Current therapies however have failed to eliminate postoperative morbidity and mortality. Multimodal techniques by their very nature are time and resource consuming. And there has not been any single technique or pharmaceutical treatment that can match such multimodal therapy. Because of these shortfalls, there is a need for new treatments for improving postoperative recovery.

IV. SUMMARY

The present invention is based on the production and use of blood products for treating symptoms and conditions impacting surgical recovery including, for example, pain and wound healing. The present invention recognizes, among other things, the need for new therapies for the treatment of unwanted conditions associated with postoperative recovery, and for improving such recovery. Derived from blood and blood plasma, the present compositions of the invention relate to a solution for the failures and shortcomings of current therapies through utilization of blood plasma fractions exhibiting efficacy in the treatment of unwanted conditions associated with postsurgical recovery and for improving such recovery.

The present invention also is based on the production and use of blood products for treating symptoms and conditions associated with acute and chronic pain. The present invention recognizes, among other things, the need for new therapies for alleviating pain. Although therapeutics exist for treating acute and chronic pain, many such therapies such as opioid analgesics present a high incidence of addiction, abuse, and associated morbidity and mortality.

V. INCORPORATION BY REFERENCE

All publications and patent applications mentioned in this specification are herein incorporated by reference to the same extent as if each individual publication or patent application was specifically and individually indicated to be incorporated by reference.

VI. BRIEF DESCRIPTION OF THE DRAWINGS

FIG. 1 depicts a chronic constrictive injury (CCI) experiment. Twenty-three-month-old wild type mice were administered a CCI or sham surgery via ligation 24 hours prior to administration of a 7-consecutive-day pulse dosing regimen of either PPF1, Gabapentin, recombinant human albumin (rhAlb) or vehicle control. Behavior was assessed during weeks two through five, and tissue collection for histology occurred during week five.

Figure 2:
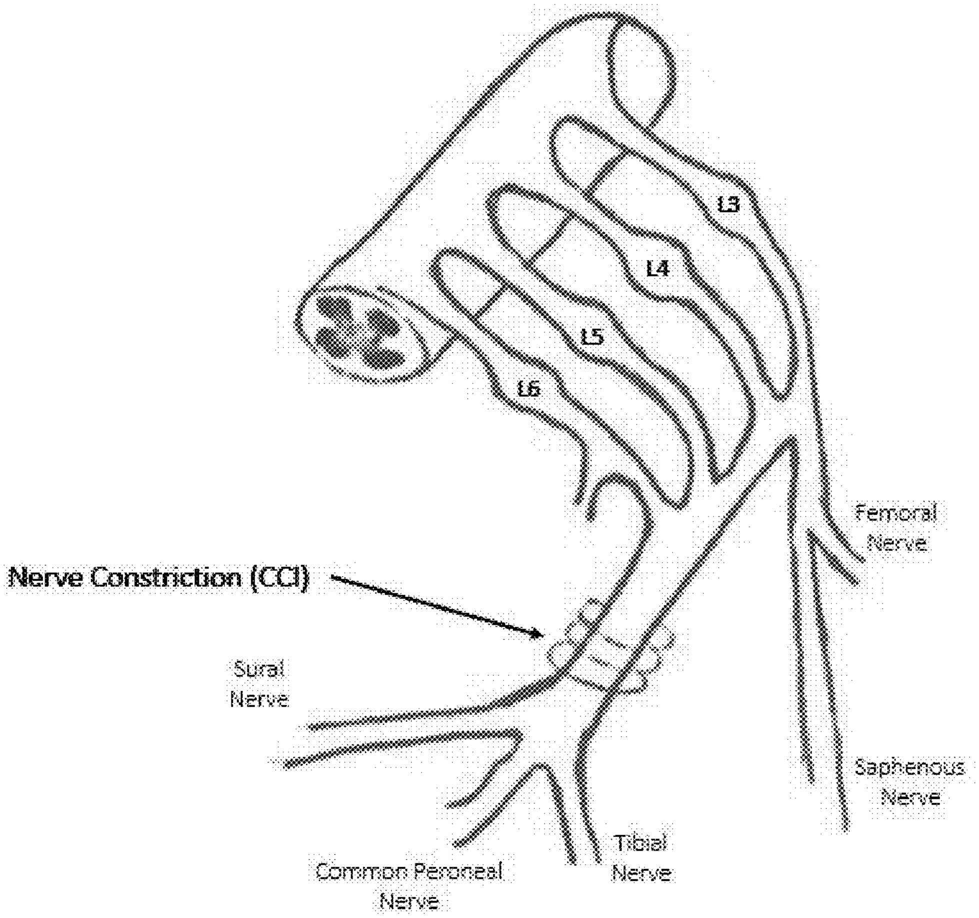

FIG. 2 is a representation depicting the location of the CCI administered to twenty-two-month-old wild type mice. The ligation was administered on the sciatic nerve as indicated by the figure. The figure was adapted from Suter M R, et al., *Anesthesiology Res and Practice*, (2011), which is incorporated herein by reference in its entirety.

Figure 3:
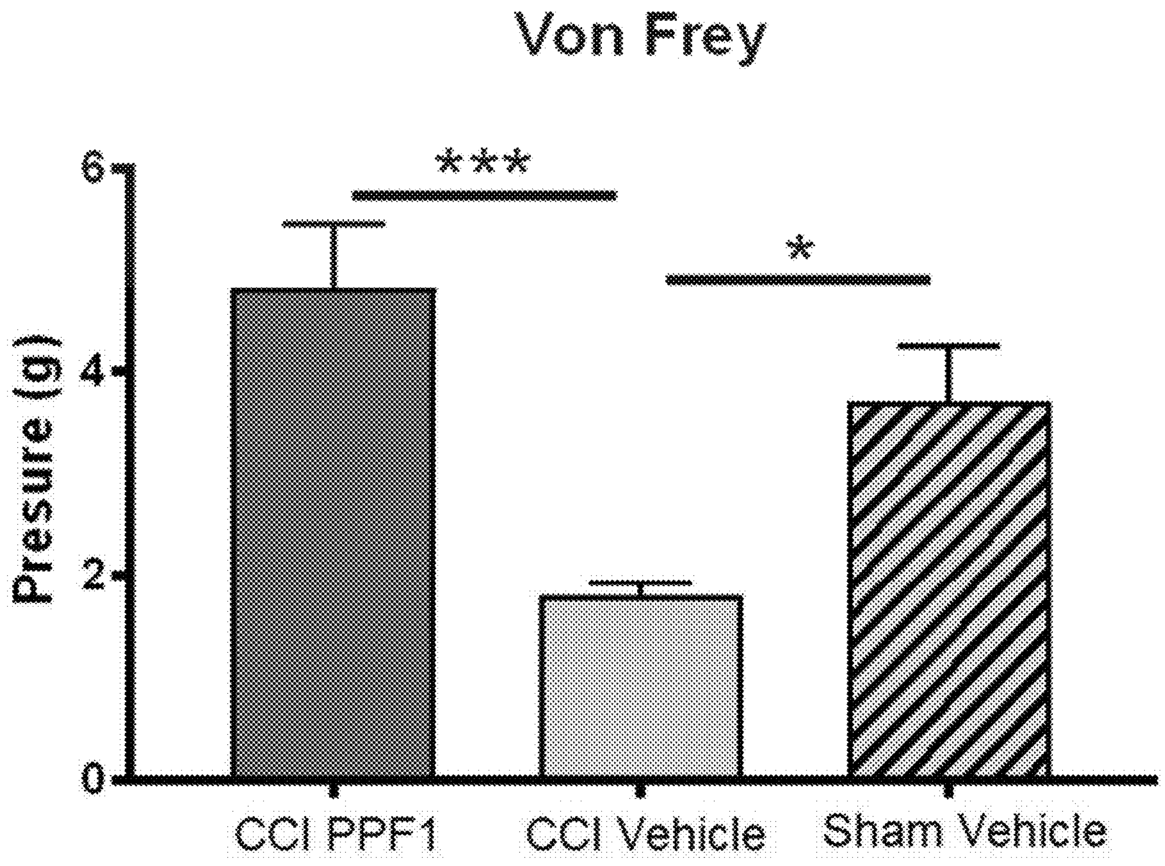

FIG. 3 reports data from a mechanical von Frey allodynia test in wild-type mice treated with CCI or sham surgery described in FIG. 1. Useful for the analysis of pain behavior, the hind paw enervated by the subject sciatic nerve, was administered with von Frey filament stimulation. The pressure at which the mouse withdrew its hind paw was measured and plotted in FIG. 3. The figure shows that mice treated with PPF1 after CCI exhibited significantly less pain (could withstand more pressure) than those treated with vehicle control after CCI. And sham operations treated with vehicle also exhibited significantly less pain that those treated with vehicle control after CCI. This shows that PPF1 has a positive effect on mechanical nociception deficits.

Figure 4:
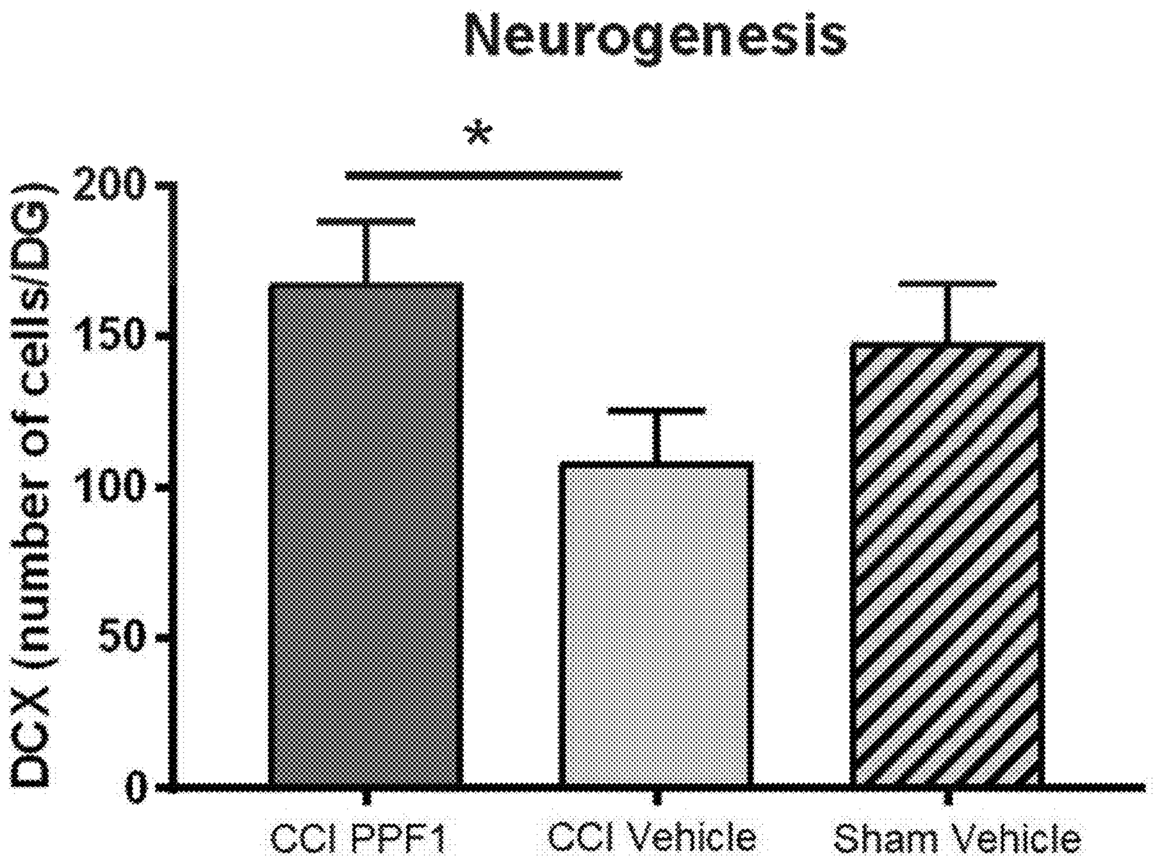

FIG. 4 reports data from hippocampal histology performed on the wild type mice described in FIG. 1. Neurogenesis was measured using the doublecortin (DCX) marker. Mice given CCI who were treated with PPF1 had significantly more neurogenesis in the hippocampus than those who received vehicle. Mice given sham operations plus vehicle trended towards greater neurogenesis than mice given CCI and vehicle post-surgery. Thus, PPF1 exhibited the ability to restore neurogenesis after chronic nerve injury.

Figure 5:
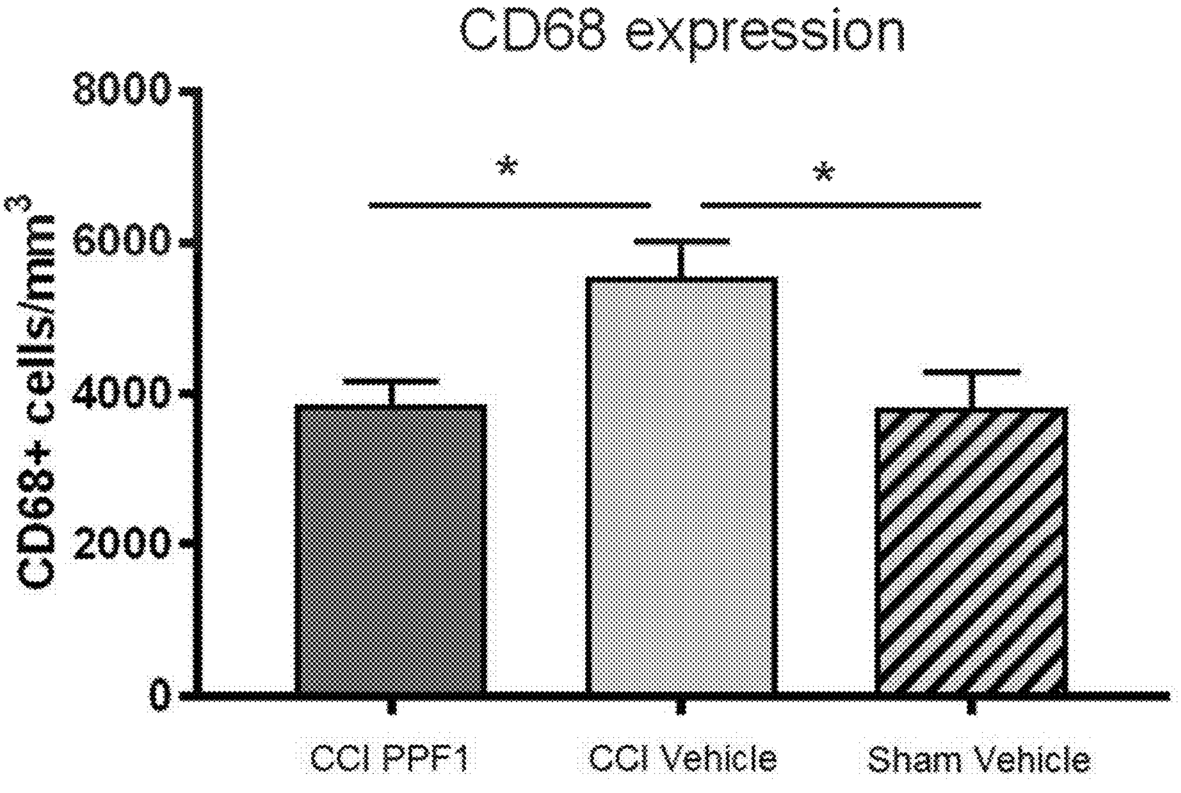

FIG. 5 reports data from hippocampal histology performed on the wild type mice described in FIG. 1. CD68 expression was quantified, and mice given a CCI plus vehicle expressed a significantly greater number of CD68 positive cells in the hippocampus than those given a CCI plus PPF1. A similar degree of difference was observed between mice given a CCI plus vehicle and those given a sham surgery plus vehicle. This shows that PPF1 can help to block neuroinflammation resulting from chronic nerve injury.

Figure 6:
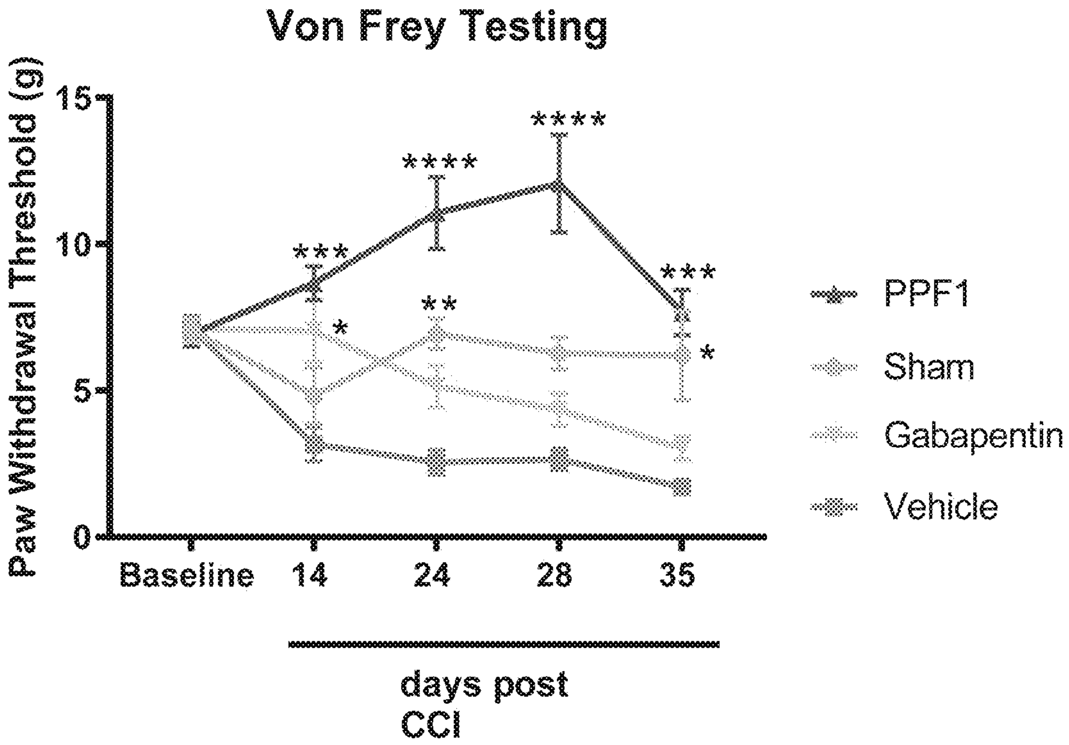

FIG. 6 reports data from a mechanical von Frey allodynia test in twenty-two-month-old C57BL/6J mice which received CCI or sham surgery and tested in the timeline as described in FIG. 1. The pressure at which the mouse withdrew its hind paw was assessed and represented in FIG. 6 as weeks post CCI or sham surgery. The figure illustrates that mice administered PPF1 following CCI surgery had significantly increased tolerance to mechanical nociception at all assessed timepoints than those treated with vehicle after CCI. Conversely, mice administered Gabapentin only show significant improvement in mechanical nociception at 2 weeks following CCI surgery and are similar to vehicle treated mice at all other timepoints. Sham surgery mice show significantly increased response to mechanical nociception at 3 and 5 weeks following surgical manipulation. Together, these data illustrate that PPF1 ameliorates peripheral pain for a greater amount of time than that of standard of care treatments (Gabapentin).

Figure 7:
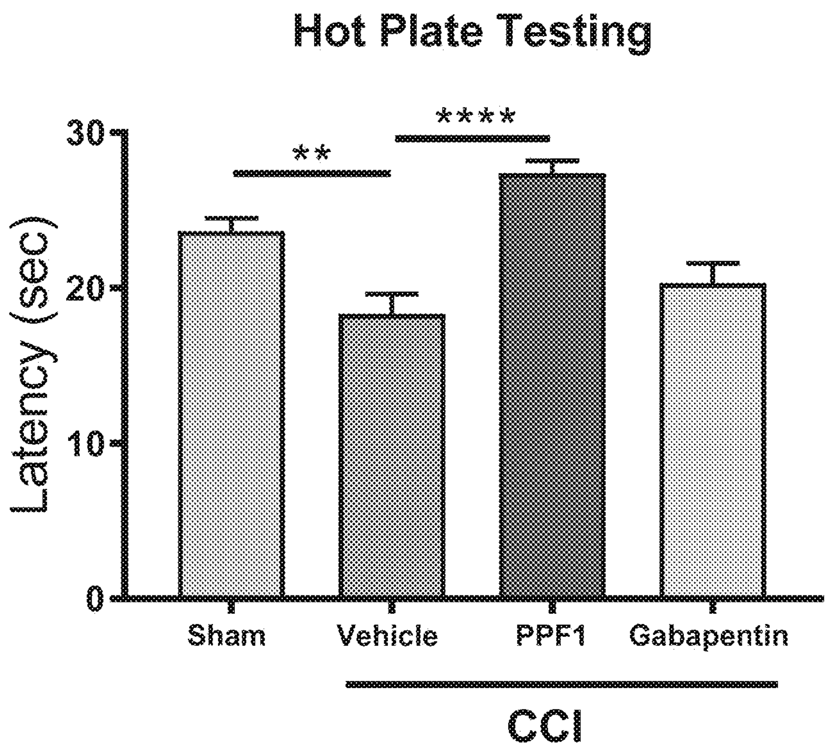

FIG. 7 reports data from a hot plate test on twenty-two-month-old wild-type mice which received CCI or sham surgery and tested in the timeline as described in FIG. 1. This assay was performed as described by Woolfe and Macdonald. (Woolfe G. and Macdonald A D, *J. Pharrnacol. Exp. Ther.* 80:300-07 (1944), which is incorporated by reference herein in its entirety). The hot plate is set to a temperature of 55° C. Mice are acclimated to being placed inside a clear cylinder for 30 minutes. The cylinder is placed upon the hot plate and a timer started. When nocifensive behaviors (e.g. hind paw licking or jumping) are first observed, the time is recorded as latency. FIG. 7 illustrates hot plate nocifensive latency 5 weeks after CCI or sham surgery. PPF1 treatment are significantly less sensitive to hot plate stimuli compared to mice given CCI plus vehicle control, indicating a rescue effect by PPF1. Whereas, standard of care effects (Gabapentin) are similar to that of vehicle.

Figure 8:
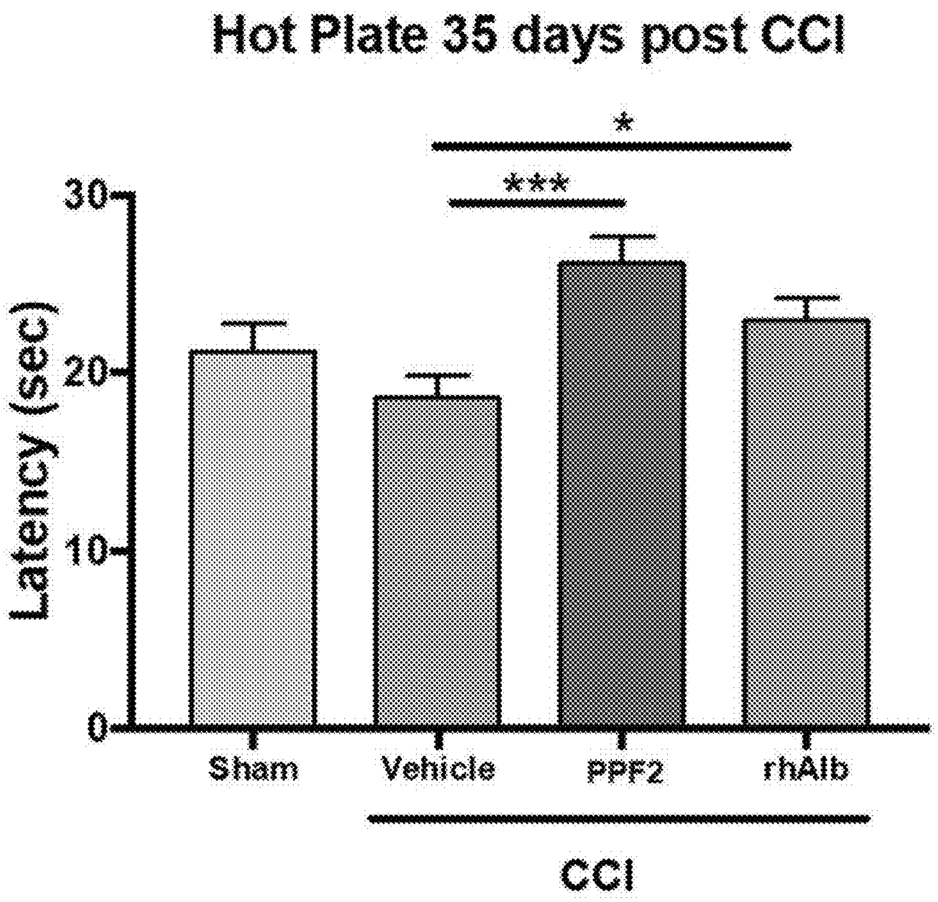

FIG. 8 reports data from a hot plate test on wild-type mice which received CCI or sham surgery and tested in the timeline as described in FIG. 1. FIG. 8 illustrates hot plate nocifensive latency 5 weeks after CCI or sham surgery. PPF1 treatment and rhALB are significantly less sensitive to hot plate stimuli compared to mice given CCI plus vehicle control.

Figure 9:
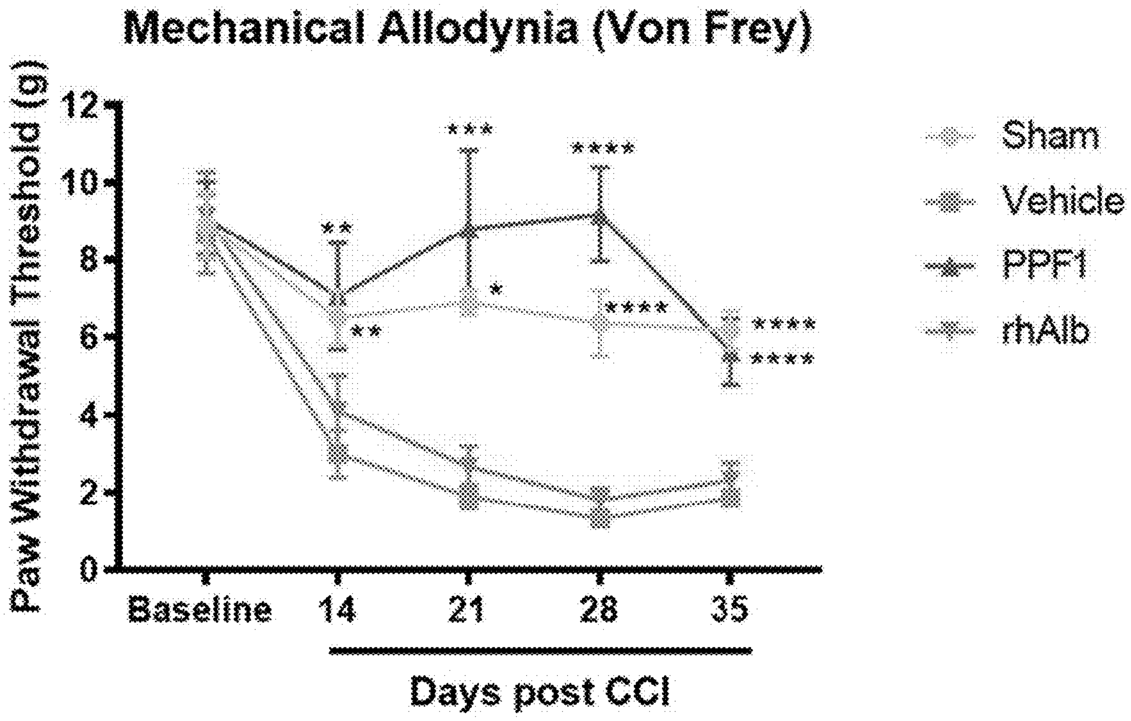

FIG. 9 reports data from a mechanical von Frey allodynia test in C57BL/6J mice which received CCI or sham surgery and tested in the timeline as described in FIG. 1. FIG. 9 illustrates that mice administered PPF1 following CCI surgery had significantly increased tolerance to mechanical nociception at all assessed timepoints than those treated with vehicle after CCI. Conversely, mice administered rhALB have similar response to mechanical allodynia to vehicle treated mice at all timepoints.

Figure 10:
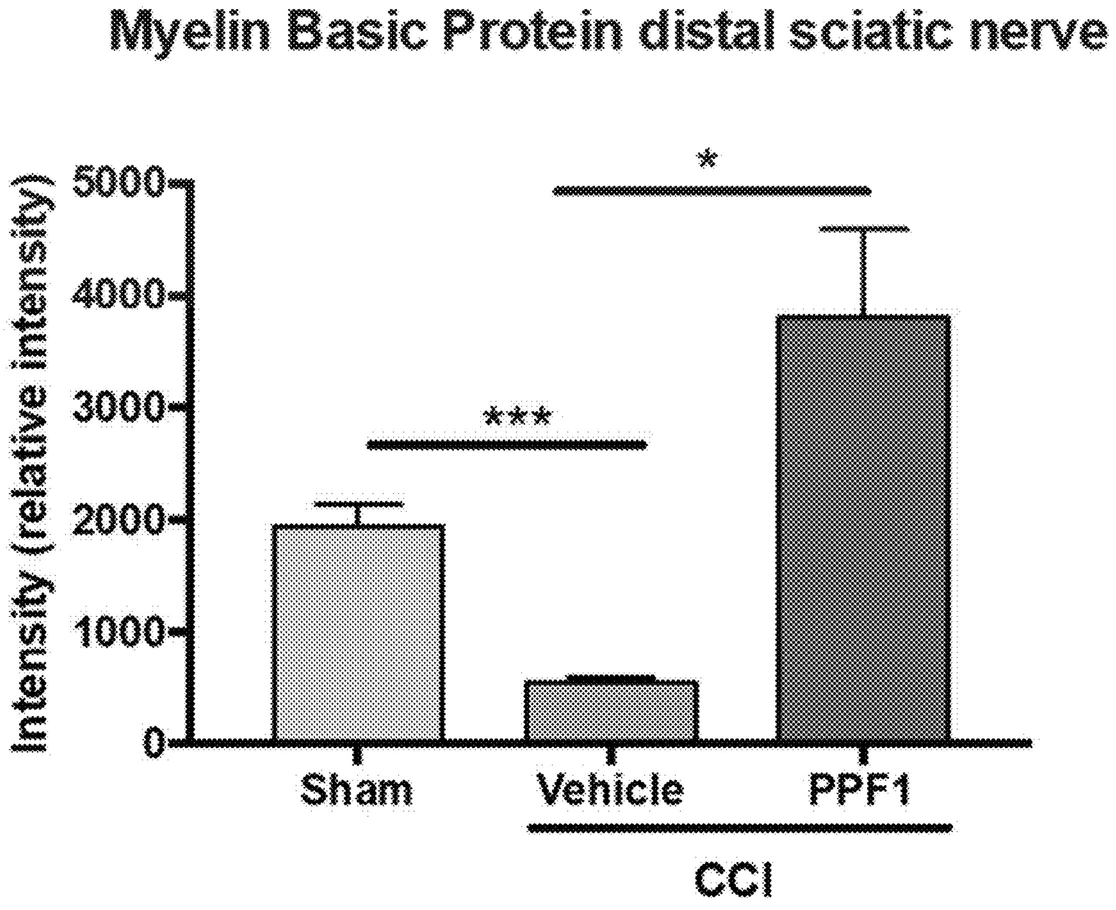

FIG. 10 reports data from sciatic nerve histological analysis (approximately 1000 μm distal from the last ligature) of myelin basic protein (MBP) expression in C57BL/6J mice which received CCI or sham surgery and analyzed following tissue collection after day 35 as described in FIG. 1. FIG. 10 illustrates that mice administered PPF1 following CCI surgery had significantly increased MBP intensity, indicative of increased myelin expression as compared to vehicle treated animals. Sham mice also express increased MBP as compared to CCI injured vehicle mice.

Figure 11:
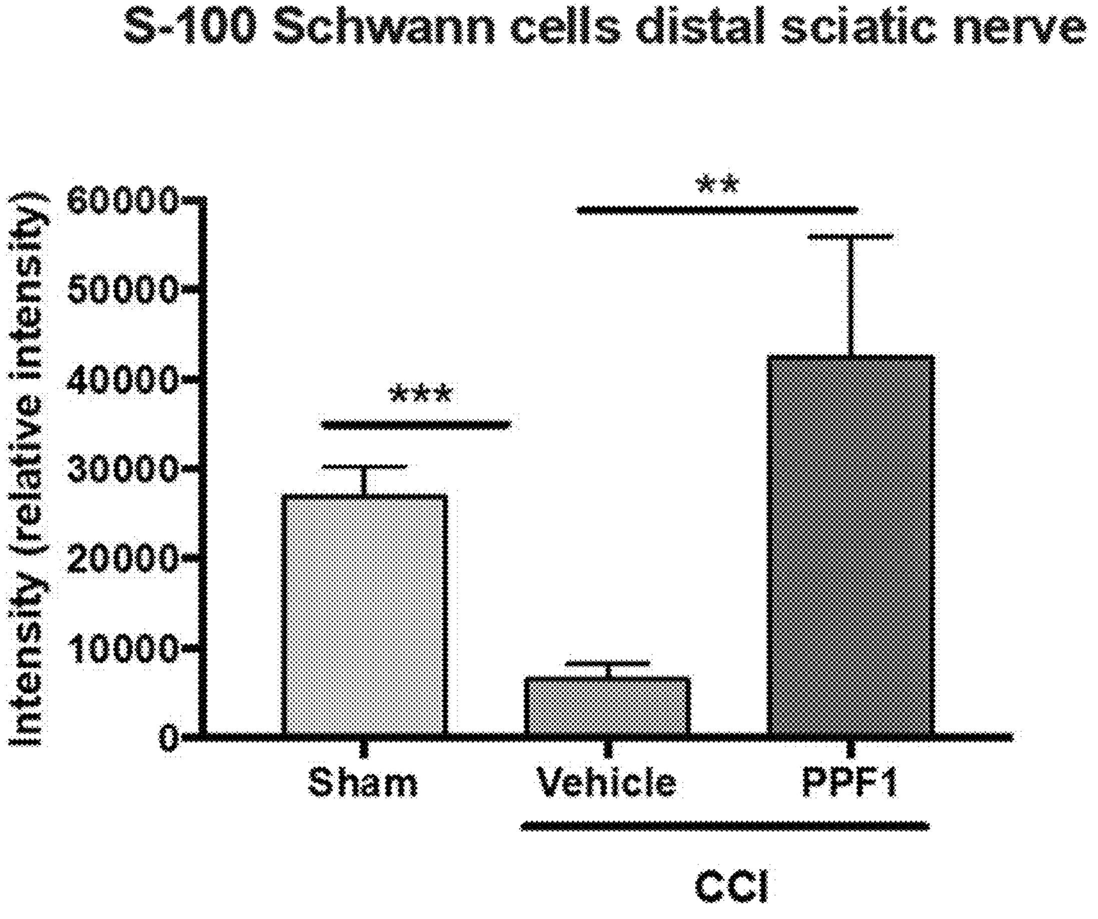

FIG. 11 reports data from sciatic nerve histological analysis (approximately 1000 μm distal from the last ligature) of S-100 protein (expressed by Schwann cells) in C57BL/6J mice which received CCI or sham surgery and analyzed following tissue collection after day 35 as described in FIG. 1. FIG. 11 illustrates that mice administered PPF1 following CCI surgery had significantly increased S-100 intensity, indicative of increased Schwann cells (which are myelin producing cells in peripheral nerves) as compared to vehicle treated animals. Sham mice also express increased S-100 as compared to CCI injured vehicle mice.

Figure 12:
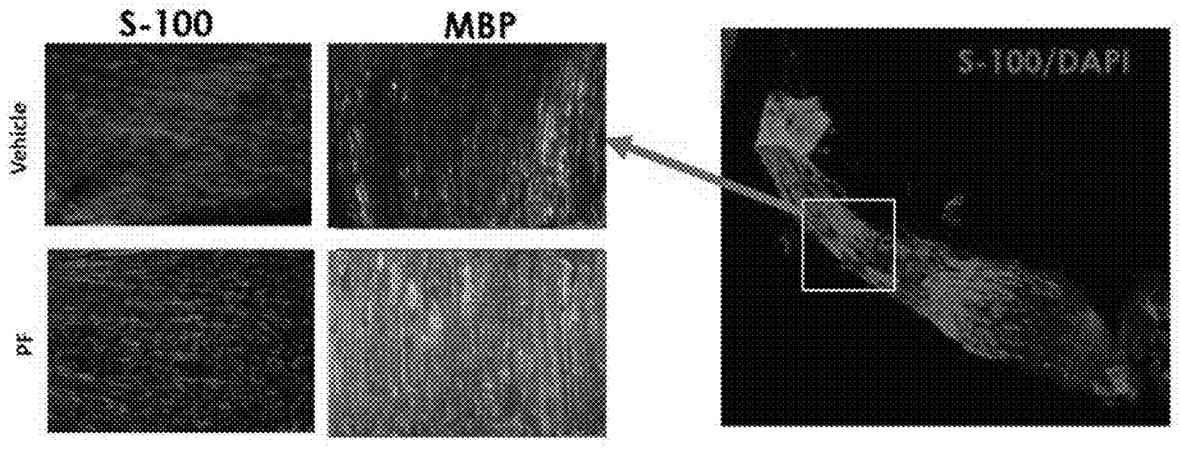

FIG. 12 are images selected from sciatic nerve histological analysis which identify the location used for quantification in FIGS. 10 and 11 (approximately 1000 μm distal from the last ligature) and representative intensities of S-100 protein (expressed by Schwann cells) and Myelin Basic Protein in C57BL/6J mice which received CCI surgery and were treated with either vehicle or PPF1 and used for qualitative analysis of sciatic nerve tissue after day 35 as described in FIG. 1.

Figure 13:
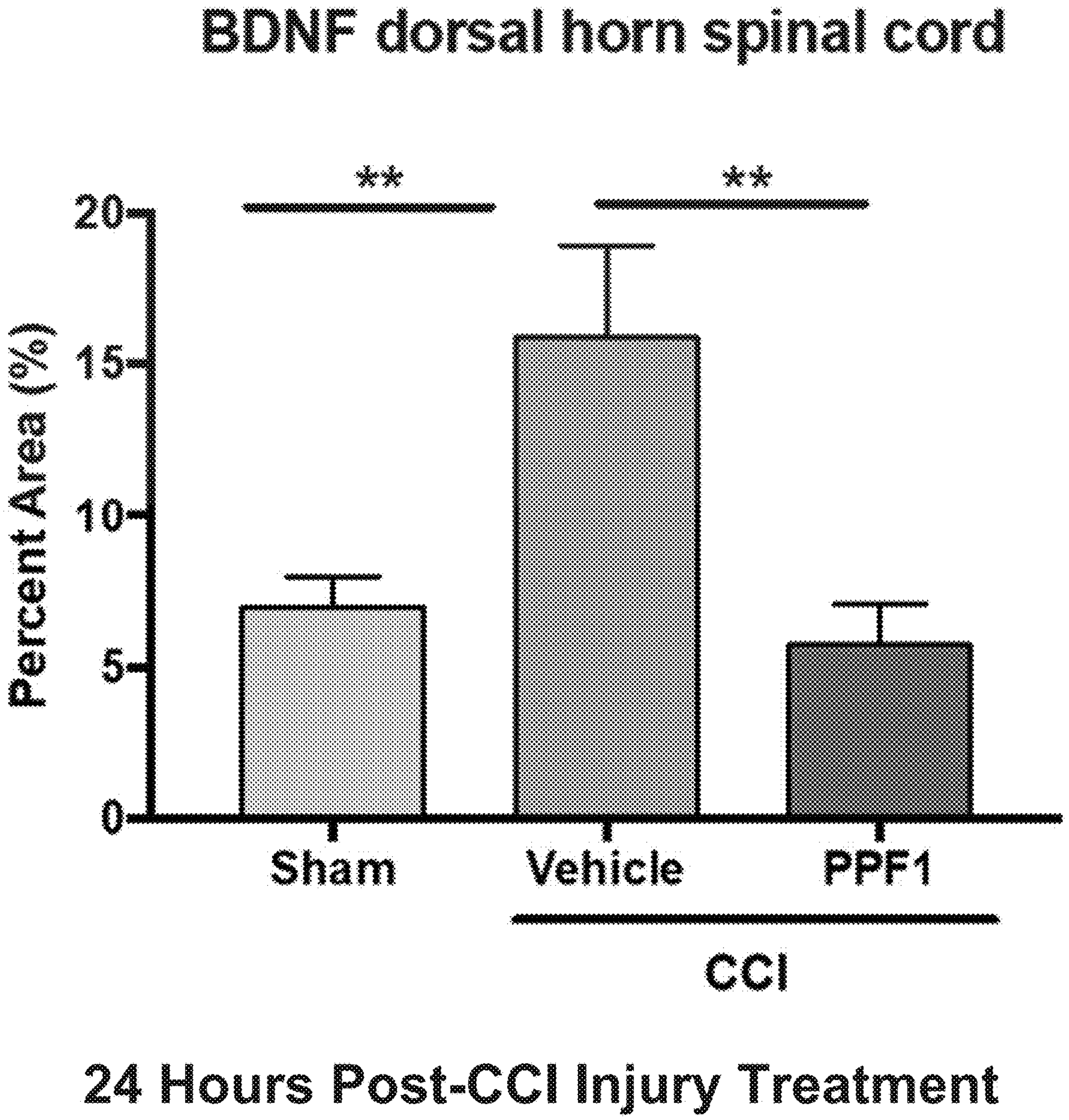

FIG. 13 reports data from spinal cord histological analysis (performed on spinal cord tissue collected from the lumbar section L4-L6) of C57BL/6J mice which received CCI or sham surgery and analyzed following tissue collection after day 35 as described in FIG. 1. FIG. 13 illustrates that mice administered PPF1 following CCI surgery had significantly decreased BDNF intensity within the dorsal horns of the spinal cord, indicative of decreased activation of microglia within the spinal cord. As BDNF is a pro-inflammatory cytokine released by activated microglia, these findings suggest that PPF1 is decreasing a fundamental regulator of pain states within the spinal cord, normalizing the level to that of sham (non-CCI injured) mice.

Figure 14:
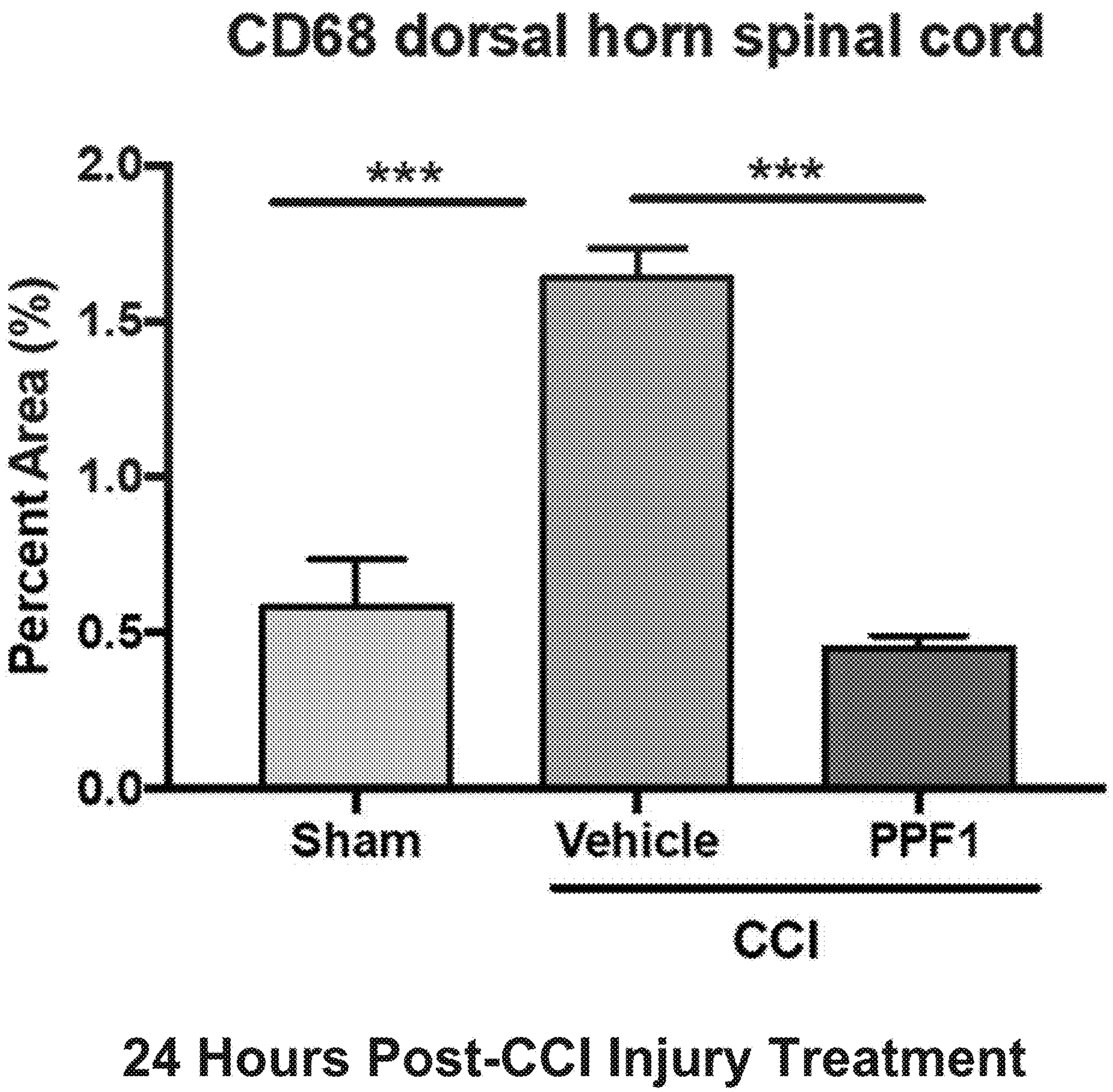

FIG. 14 reports data from spinal cord histological analysis (performed on spinal cord tissue collected from the lumbar section L4-L6) of C57BL/6J mice which received CCI or sham surgery and analyzed following tissue collection after day 35 as described in FIG. 1. FIG. 14 illustrates that mice administered PPF1 following CCI surgery had significantly decreased CD68 intensity within the dorsal horns of the spinal cord, indicative of decreased activation of microglia within the spinal cord. As CD68 protein is expressed by activated microglia, this suggests that PPF1 is decreasing the activation of the fundamental cell type responsible for induction of pain states within the spinal cord, normalizing the level to that of sham (non-CCI injured) mice. Data presented in FIG. 13 and FIG. 14 indicate that PPF1 is centrally regulating the pain state resulting from sciatic nerve injury and ameliorating or preventing the establishment of pain signaling between the peripheral nerves and the brain, also described as central sensitization.

Figure 15:
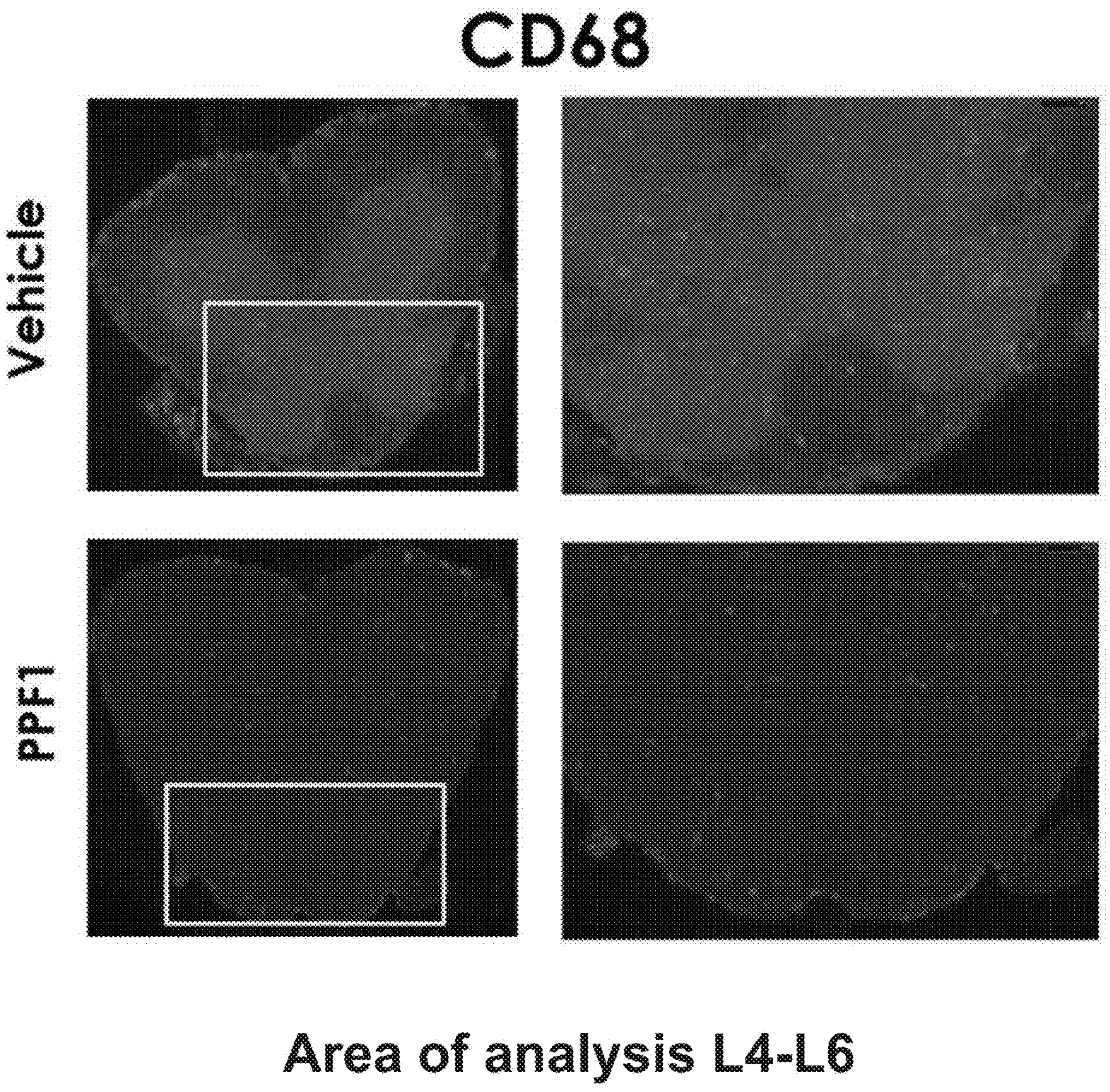

FIG. 15 are images selected from spinal cord histological analysis which identify the location of dorsal horns used for quantification in FIG. 14 (performed on spinal cord tissue collected from the lumbar section L4-L6) and representative intensities of CD68 protein (expressed by activated microglia) in C57BL/6J mice which received CCI surgery and were treated with either vehicle or PPF1 and used for qualitative analysis of spinal cord tissue after day 35 as described in FIG. 1.

Figure 16:
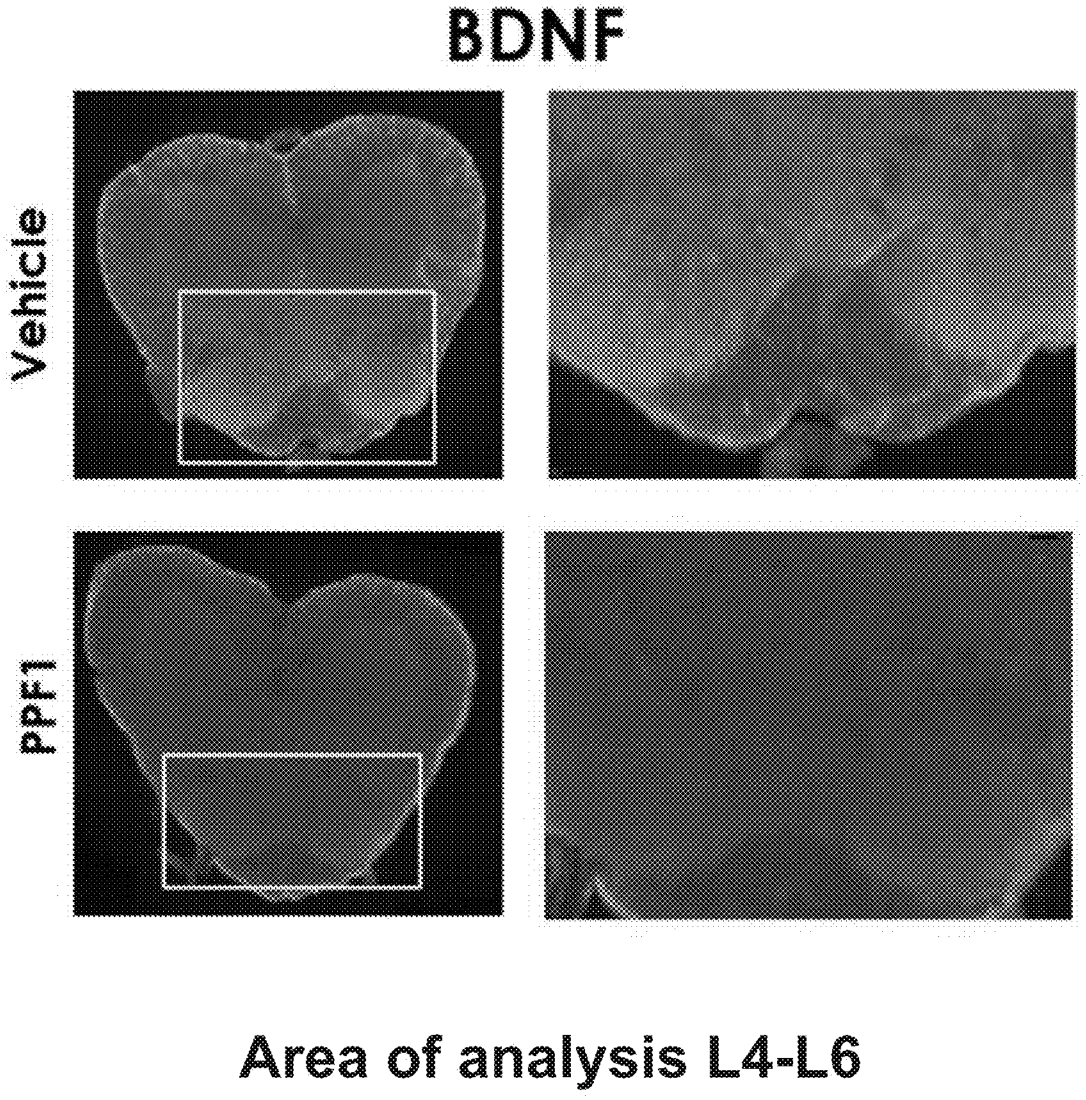

FIG. 16 are images selected from spinal cord histological analysis which identify the location of dorsal horns used for quantification in FIG. 13 (performed on spinal cord tissue collected from the lumbar section L4-L6) and representative intensities of BDNF protein (a cytokine released by activated microglia) in C57BL/6J mice which received CCI surgery and were treated with either vehicle or PPF1 and used for qualitative analysis of spinal cord tissue after day 35 as described in FIG. 1.

Figure 17:
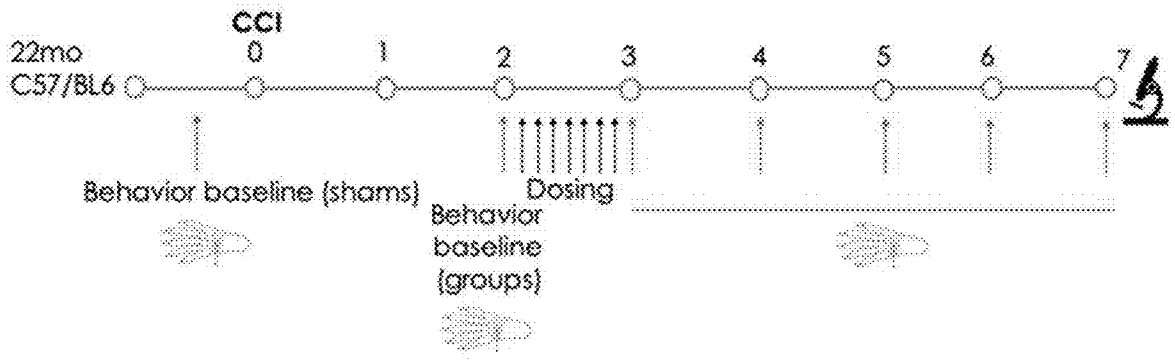

FIG. 17 depicts a chronic constrictive injury (CCI) experiment. Twenty-two-month-old wild type mice were administered a CCI or sham surgery via ligation 2 weeks prior to administration of a 7-consecutive-day pulse dosing regimen of either PPF1, rhALB or vehicle control. Behavior was assessed weekly during weeks two through seven, and tissue collection for histology occurred during week seven.

Figure 18:
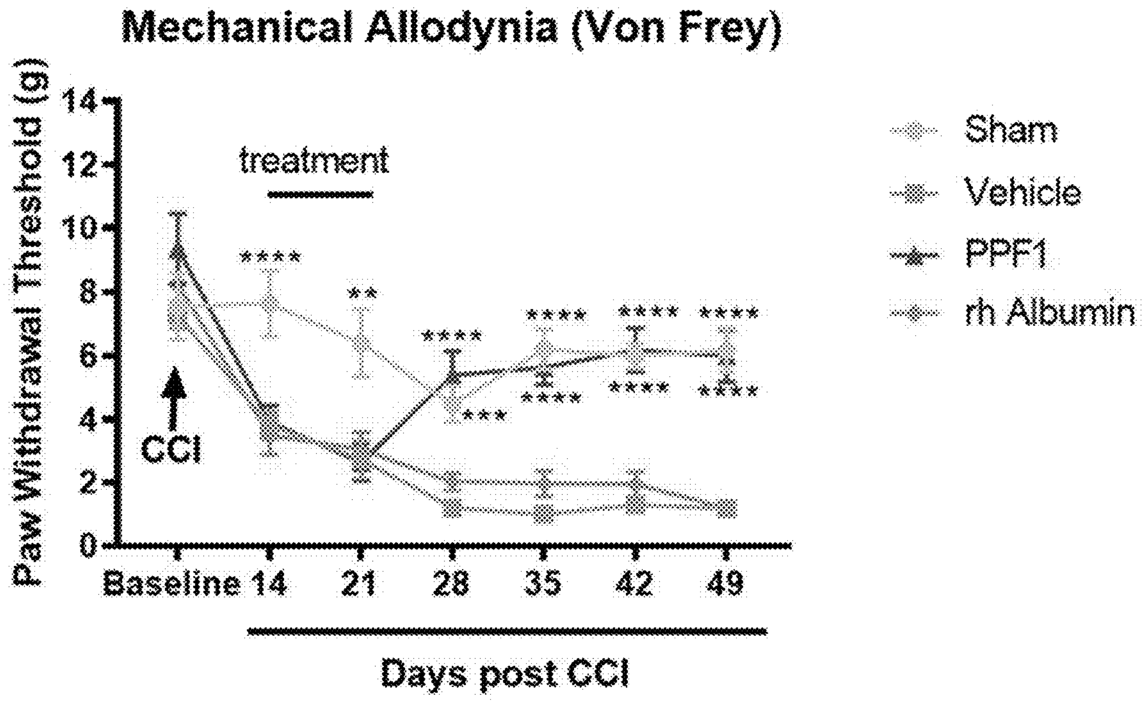

FIG. 18 reports data from a mechanical von Frey allodynia test in C57BL/6J mice which received CCI or sham surgery and tested in the timeline as described in FIG. 17. FIG. 18 illustrates that mice administered PPF1 two weeks following CCI surgery had significantly increased tolerance to mechanical nociception beginning at a timepoint one week following the cessation of PPF1 treatment which was maintained throughout the duration of the study. Findings in FIG. 18 suggest that PPF1 treatment initiates processes which reduce sensitivity to mechanical allodynia in a longitudinal fashion, as improved tolerance isn't evidenced until a week following treatment (in contrast with therapies which exclusively provide benefit during treatment, such as opioid analgesics) and is sustained for at least 28 days. Conversely, mice administered rhALB have similar response to mechanical allodynia to vehicle treated mice at all timepoints.

Figure 19:
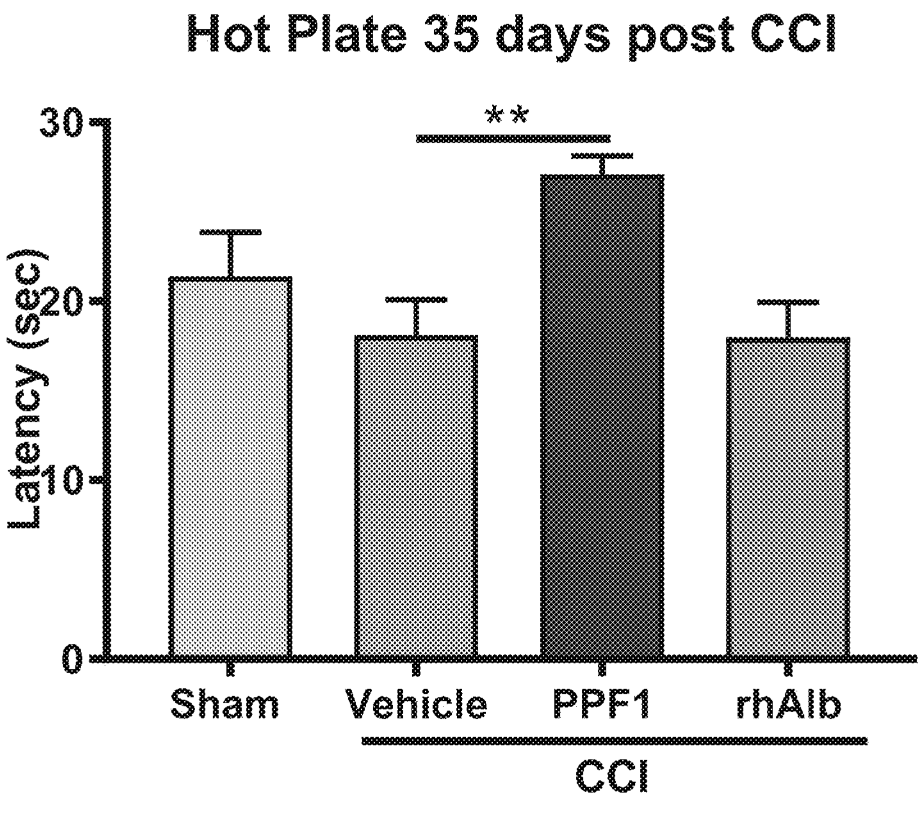

FIG. 19 reports data from a hot plate test on wild-type mice which received CCI or sham surgery and tested in the timeline as described in FIG. 17. FIG. 19 illustrates hot plate nocifensive latency 5 weeks after CCI or sham surgery. PPF1 treatment is significantly less sensitive to hot plate stimuli compared to mice given CCI plus vehicle control.

Figure 20:
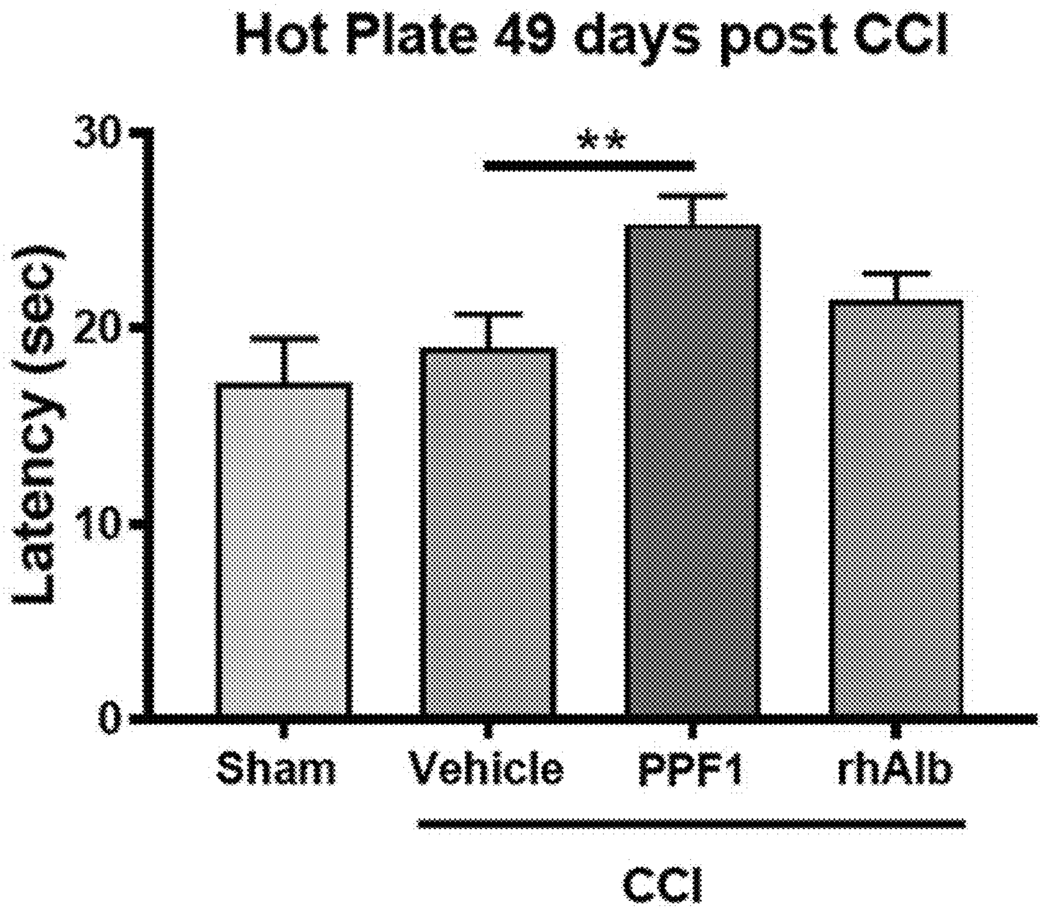

FIG. 20 reports data from a hot plate test on wild-type mice which received CCI or sham surgery and tested in the timeline as described in FIG. 17. FIG. 20 illustrates hot plate nocifensive latency 7 weeks after CCI or sham surgery. PPF1 treatment is significantly less sensitive to hot plate stimuli compared to mice given CCI plus vehicle control.

Figure 21A:
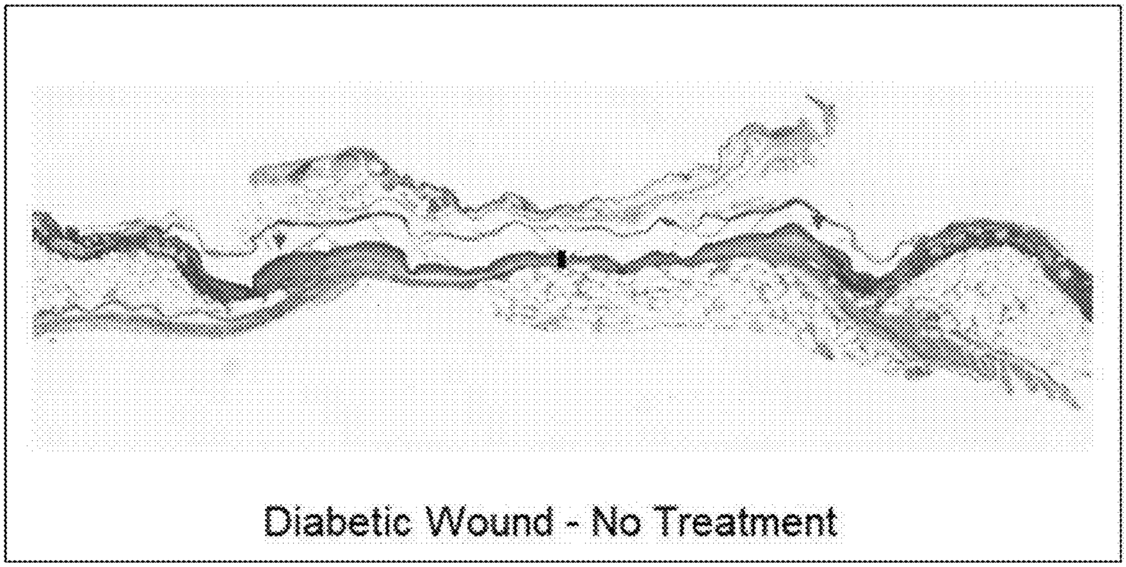
Figure 21B:
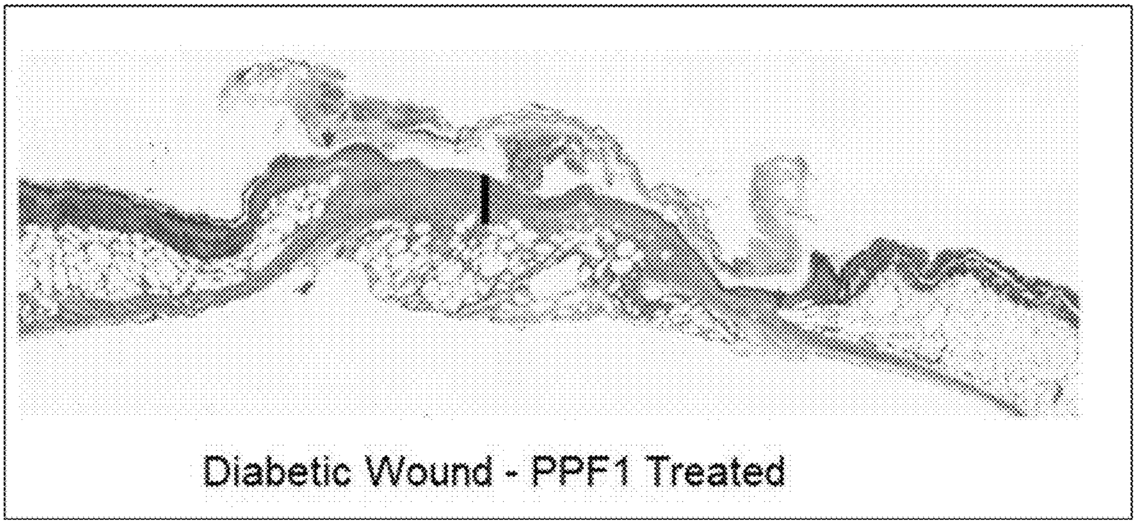

FIGS. 21A and 21B provide a histological comparison between a diabetic wound (B6.BKS(D)-Lepr$^{db}$/J diabetic mouse model) that was untreated (FIG. 21A) or with PPF1 (FIG. 21B). Black bars indicate wound bed thickness (epidermal plus granulation layer). Arrows indicate wound boundaries. Wound bed thickness was increased in PPF1-treated mice as determined by wound bed thickness. PPF1 therefore demonstrates improved wound healing.

Figure 22A:
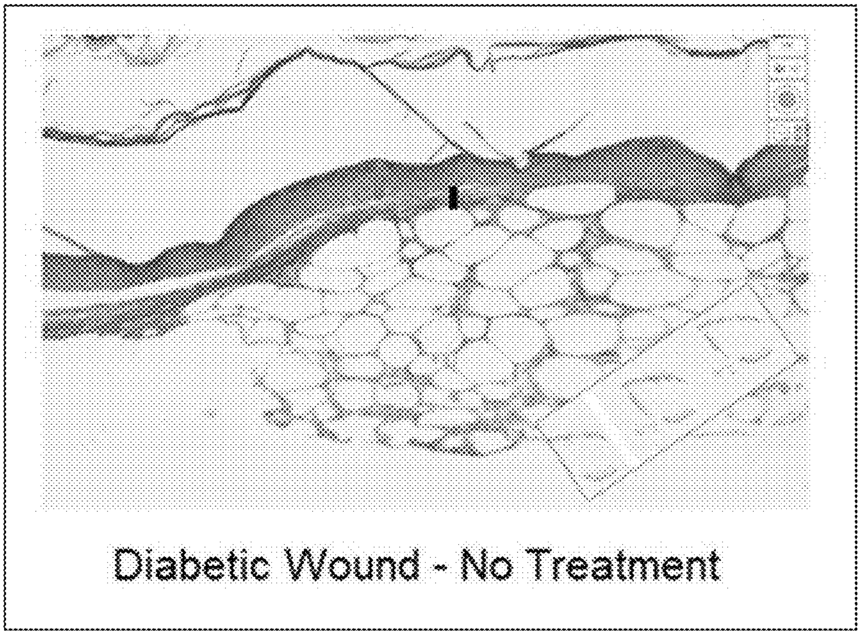
Figure 22B:
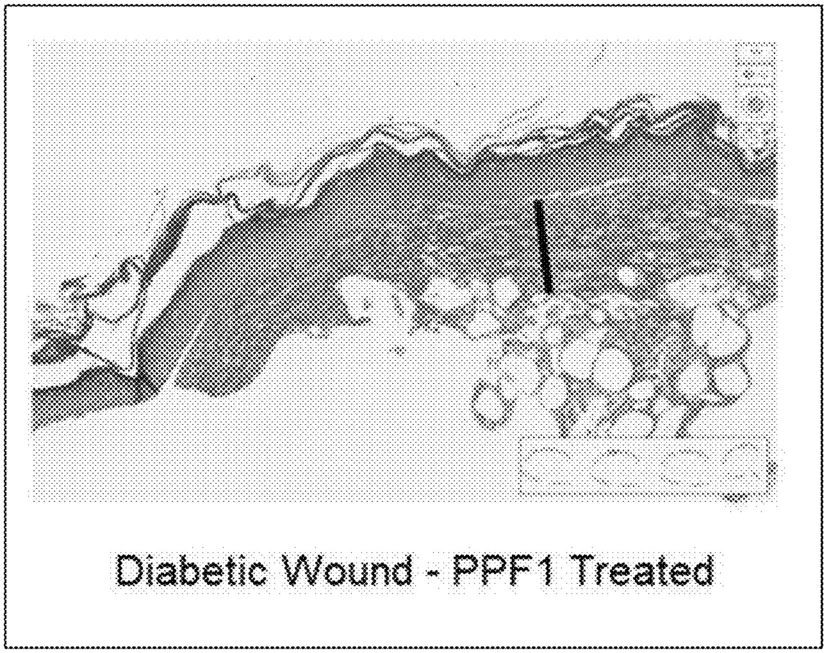

FIGS. 22A and 22B is a histological comparison between a diabetic wound (B6.BKS(D)-Lepr$^{db}$/J diabetic mouse model) that was untreated (FIG. 22A) or with PPF1 (FIG. 22B). Black bars indicate the granulation layer. Blue bars indicate the epidermal layer. The PPF1-treated wound exhibited a thicker epidermal layer than the untreated wound, however the granulation layer exhibited an even greater trend in the difference between PPF1-treated and untreated wounds (i.e. the granulation layer was thicker in the PPF1-treated wounds than the untreated wounds).

Figure 23:
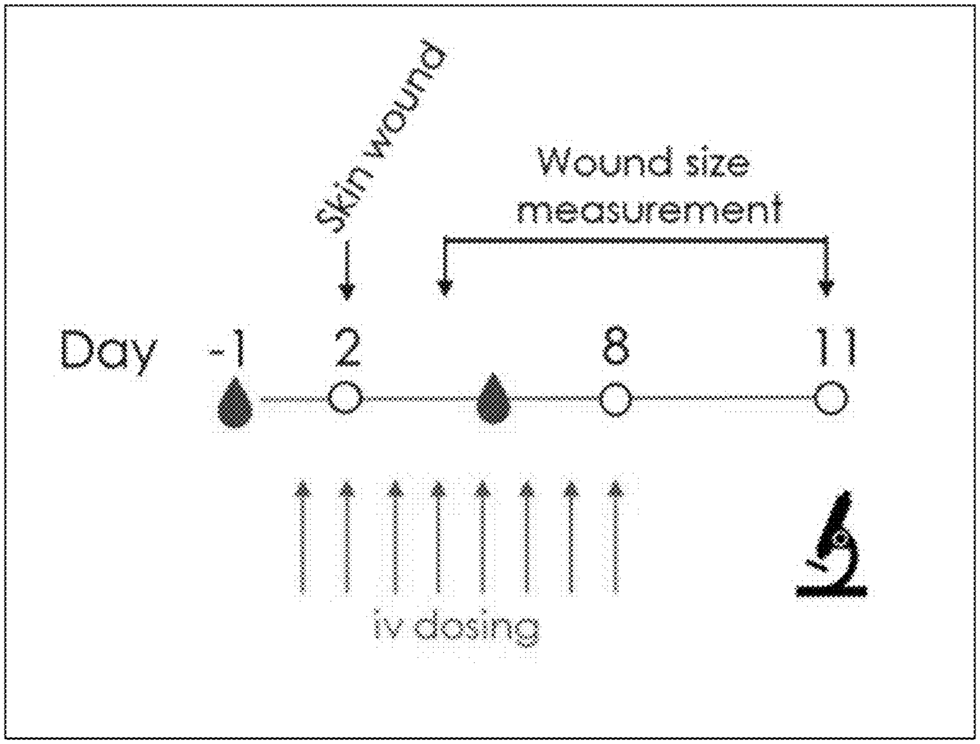

FIG. 23 depicts the general design of the diabetic wound healing experiment used in FIGS. 24 through 28. Blood drops indicate when blood was collected to measure fasting glucose level. On Day 2, the skin wound was made, and on Days 1-7 intravenous (iv) dosing was performed. Histology (signified by the microscope) was performed after sacrifice.

Figure 24:
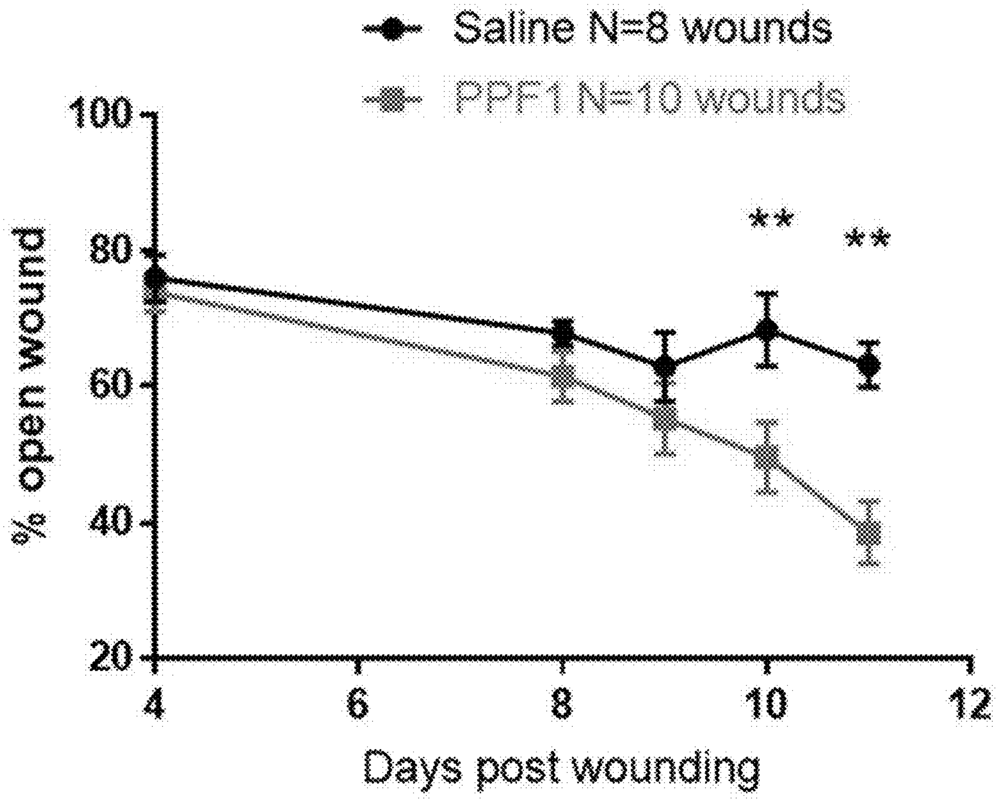

FIG. 24 reports the percentage of the wound still open at several time points post-wounding in a first study (Study 1). Mice were treated with either PPF1 (150 μL) for 7 days or saline control. After 10 days, the sizes of the open wounds in PPF1-treated animals was significantly reduced compared to saline control. (** $p<0.006$ by unpaired T-test).

Figure 25:
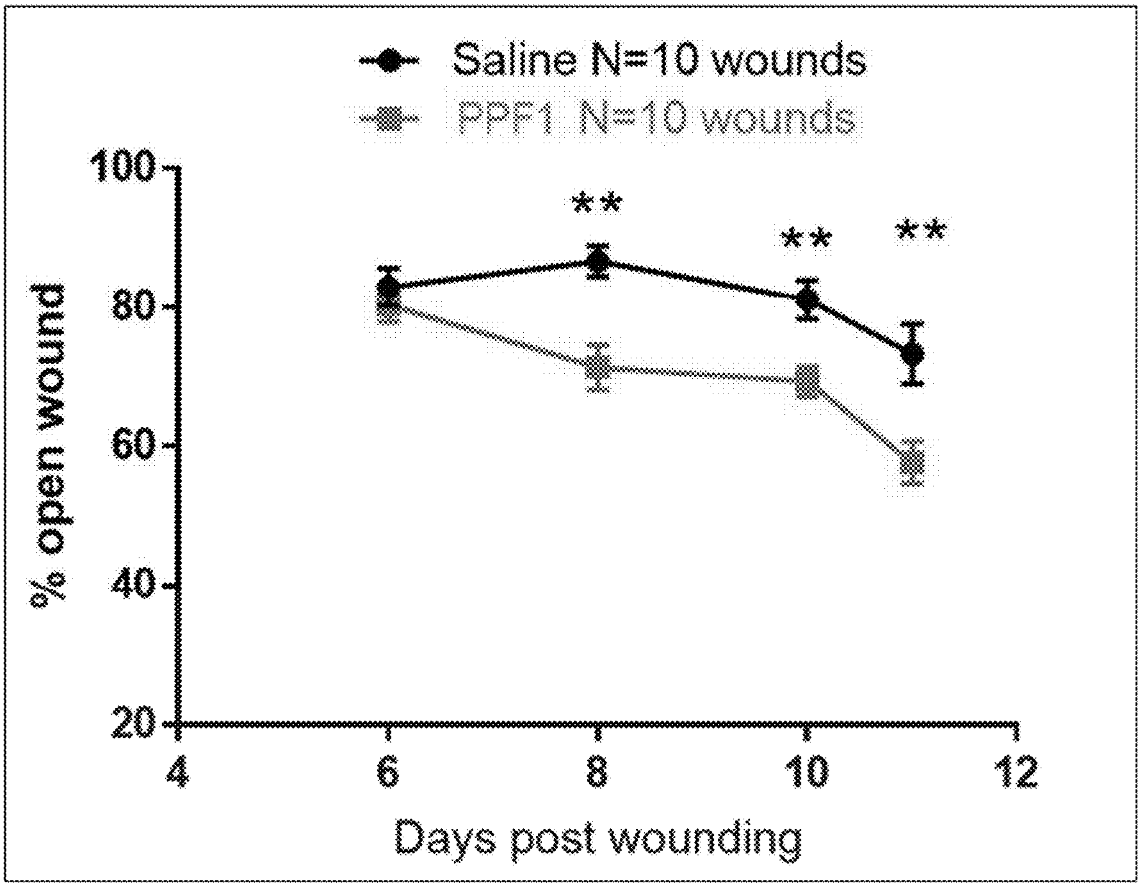

FIG. 25 reports the percentage of the wound still open at several time points post-wounding in a second similar study (Study 2). Mice were treated with either PPF1 (150 μL) for 7 days or saline control. After 8 days, the sizes of the open wounds in PPF1-treated animals was significantly reduced compared to saline control. (** $p<0.0018$ unpaired T-test).

Figure 26:
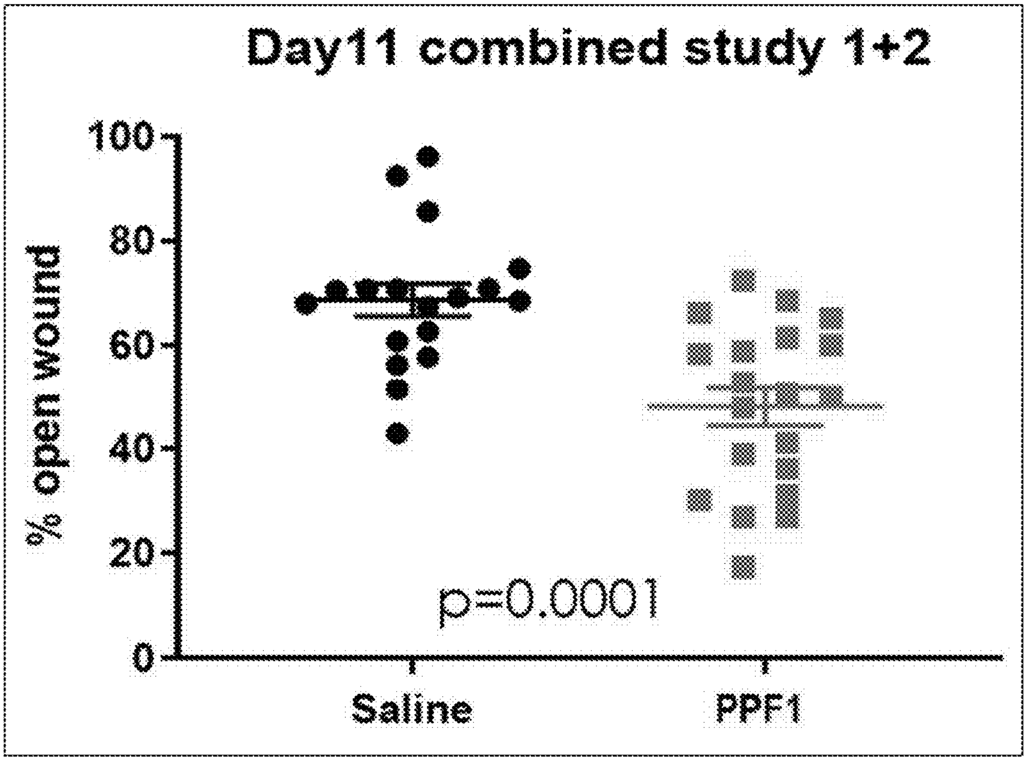

FIG. 26 reports the percentage of the wound still open at 11 days post-wounding, combining the data from Studies 1 and 2. PPF1-treated animals exhibits a statistically-significant decrease in the percentage of wound left open after 11 days. ( $p<0.006$ by unpaired T-test). The difference between PPF1-treated and vehicle-treated animals at Day 10 was similarly significant ( $p<0.006$ by unpaired T-test).

Figure 27:
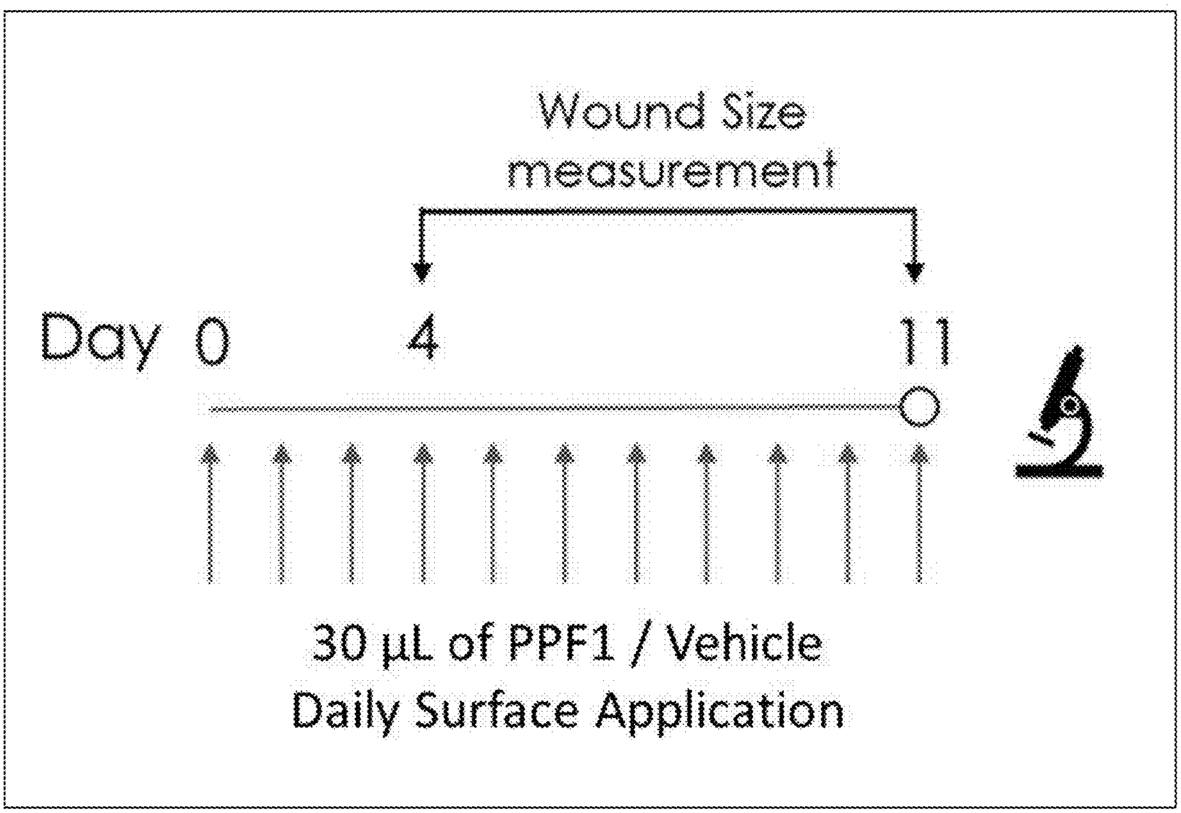

FIG. 27 reports the results of a study using topically-administered PPF1 or vehicle to wounds in B6 ob/ob (B6.Cg-Lepob/J mice). FIG. 27 shows the study paradigm of daily administrations of 30 μL of topical PPF1 or control vehicle administered to the wounds. Wounding was performed as described in FIG. 10.

Figure 28:
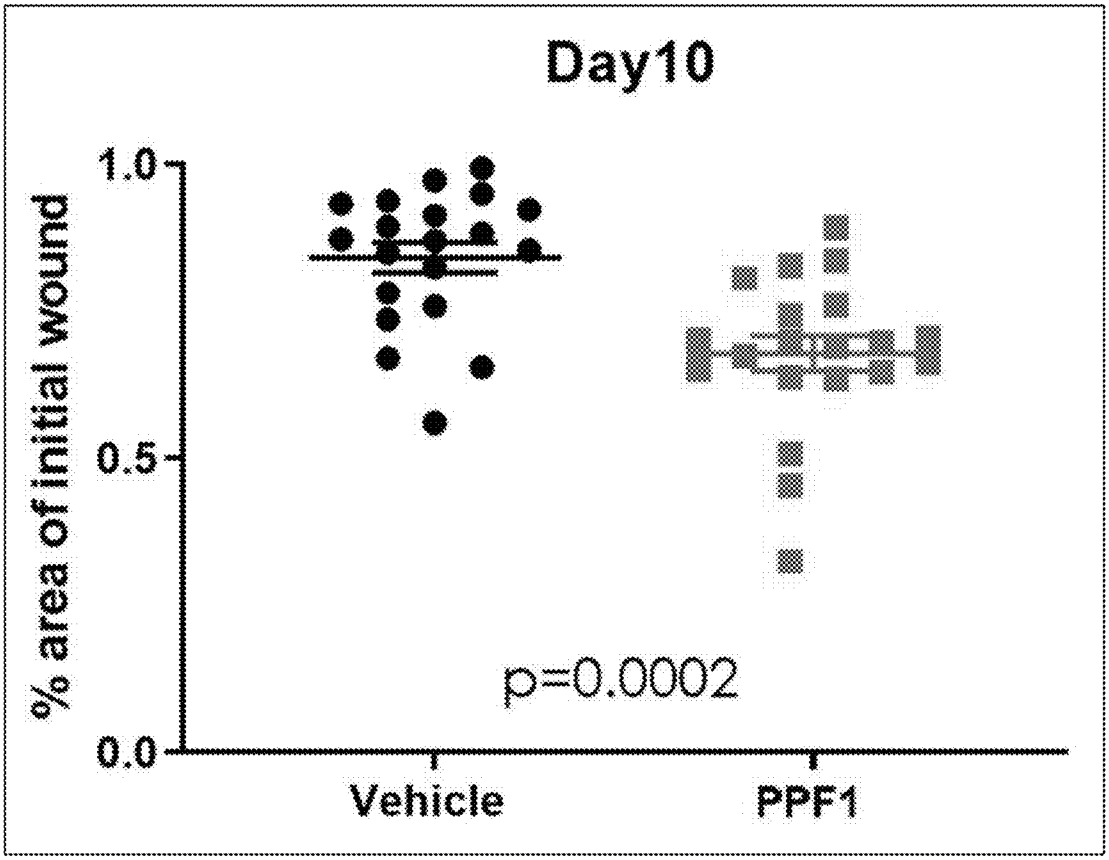

FIG. 28 reports the results of the topical study, with percentage of the area of the initial wound left after 10 days of treatment. FIG. 28 indicates that PPF1 significantly decreased percentage of the open wound left after 10 days compared to control vehicle.

VII. DETAILED DESCRIPTION OF THE INVENTION

A. Introduction

The present invention relates to the identification and discovery of methods and compositions for the treatment of unwanted conditions associated with postoperative recovery, and for improving such recovery. By "improving such recovery," it is meant that a subject's postoperative recovery may be accelerated, i.e. the subject may become mobile or be discharged from in-patient care in less time than it would take without the intervention of the embodiments of the present invention. By "unwanted conditions," it is meant a condition or symptom such as, by way of example and not limitation, pain, cardiopulmonary issues, infections, thromboembolic issues, inflammation, and delayed wound healing. Described herein are methods and compositions for the treatment of subjects suffering from unwanted conditions associated with postoperative recovery, and for improving such recovery, which are aspects of the present invention. Also described herein are dosing regimens which trigger improvement in subjects suffering from unwanted conditions associated with postoperative recovery, and for improving such recovery. The methods and compositions described herein are useful in: preventing complications from postoperative recovery; ameliorating the symptoms of preventing complications from postoperative recovery; and accelerating postoperative recovery. The methods and compositions of the invention may be utilized or administered preoperatively (before surgery); perioperatively (during surgery); or postoperatively (after surgery).

Another aspect of the invention is for treating chronic pain/neuropathy more generally, and not exclusively chronic pain/neuropathy associated with postoperative recovery. The methods and compositions of the invention described herein can be used to treat chronic pain and neuropathy. By "treating chronic pain and neuropathy" it is meant that the degree of chronic pain experienced by the subject to whom is administered the compositions of the invention is lessened, slightly, moderately, or significantly as assessed by subjective or objective means. Such means may include self- or medical professional-administered tests such as, by way of example and not limitation: X-ray; MRI, CT scans; patient rating or description of the pain; range of motion; reflexes, muscle strength; sensitivity (e.g. how long it takes for the subject to remove a limb that is subjected to pressure or other stimulus); blood tests for inflammatory markers; electromyography (EMG); and nerve conduction velocity).

An implementation of the invention includes using blood plasma fractions as treatment, such as one or more fractions or effluents obtained from blood fractionation processes, e.g., like the Cohn fractionation process described below. An embodiment of the invention includes using Plasma Fraction (a solution comprised of normal human albumin, alpha and beta globulins, gamma globulin, and other proteins either individually or as complexes, hereinafter referred to as "Plasma Fraction"). Another embodiment of the invention includes using Plasma Protein Fraction (PPF) as treatment. Another embodiment of the invention includes using Human Albumin Solution (HAS) fraction as treatment. Yet another embodiment includes using effluents from blood fractionation processes such as Effluent I or Effluent II/III described below. An additional embodiment includes a blood plasma fraction from which substantially all the clotting factors have been removed in order to retain efficacy while reducing the risk of thromboses (for example, see U.S. Patent Application Nos. 62/236,710 and 63/376,529, which are incorporated by reference in their entirety herein).

Before describing the present invention in detail, it is to be understood that this invention is not limited to a particular method or composition described, as such may, of course, vary. It is also understood that the terminology used herein is for the purpose of describing particular embodiments only, and is not intended to be limiting, since the scope of the present invention will be limited only by the appended claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It is noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein have discrete components and features which may be readily separated from or combined with the features of any of the other several embodiments without departing from the scope or the spirit of the present invention. Any recited method can be carried out in the order of events recited or in any other order which is logically possible.

B. Definitions

Unless otherwise defined, all technical and scientific terms used herein have the same meaning as commonly understood by one having ordinary skill in the art to which the invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those having skill in the art, and so forth.

In describing methods of the present invention, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). As such, subjects of the invention, include but are not limited to mammals, e.g., humans and other primates, such as chimpanzees and other apes and monkey species; and the like, where in certain embodiments the subject are humans. The term subject is also meant to include a person or organism of any age, weight or other physical characteristic, where the subjects may be an adult, a child, an infant or a newborn.

By a "young" or "young individual" it is meant an individual that is of chronological age of 40 years old or younger, e.g., 35 years old or younger, including 30 years old or younger, e.g., 25 years old or younger or 22 years old or younger. In some instances, the individual that serves as the source of the young plasma-comprising blood product is one that is 10 years old or younger, e.g., 5 years old or younger, including 1-year-old or younger. In some instances, the subject is a newborn and the source of the plasma product is the umbilical cord, where the plasma product is harvested from the umbilical cord of the newborn. As such, "young" and "young individual" may refer to a subject that is between the ages of 0 and 40, e.g., 0, 1, 5, 10, 15, 20, 25, 30, 35, or 40 years old. In other instances, "young" and "young individual" may refer to a biological (as opposed to chronological) age such as an individual who has not exhibited the levels of inflammatory cytokines in the plasma exhibited in comparatively older individuals. Conversely, these "young" and "young individual" may refer to a biological (as opposed to chronological) age such as an individual who exhibits greater levels of anti-inflammatory cytokines in the plasma compared to levels in comparatively older individuals. By way of example, and not limitation, the inflammatory cytokine is Eotaxin, and the fold difference between a young subject or young individual and older individuals is at least 1.5-fold. Similarly, the fold difference between older and younger individuals in other inflammatory cytokines may be used to refer to a biological age. (See U.S. patent application Ser. No. 13/575,437 which is herein incorporated by reference). Usually, the individual is healthy, e.g., the individual has no hematological malignancy or autoimmune disease at the time of harvest.

As used herein, "treatment" refers to any of (i) the prevention of the disease or disorder, or (ii) the reduction or elimination of symptoms of the disease or disorder. Treatment may be effected prophylactically (prior to the onset of disease) or therapeutically (following the onset of the disease). The effect may be prophylactic in terms of completely or partially preventing a disease or symptom thereof and/or may be therapeutic in terms of a partial or complete cure for a disease and/or adverse effect attributable to the disease. Thus, the term "treatment" as used herein covers any treatment of a condition associated with postoperative recovery in a mammal and includes: (a) preventing the condition from occurring in a subject; (b) inhibiting the condition, i.e., arresting its occurrence; or (c) relieving the condition, i.e., causing regression of the condition. Treatment may result in a variety of different physical manifestations, e.g., modulation in gene expression, rejuvenation of tissue or organs, decreasing inflammation, etc. The therapeutic agent may be administered before, during or after the onset of the condition. The subject therapy may be administered during the symptomatic stage of the condition, and in some cases after the symptomatic stage of the condition.

Blood Products Comprising Plasma Components. In practicing the subject methods, a blood product comprising plasma components is administered to an individual in need thereof, e.g., an individual suffering from a postoperative condition. As such, methods according to embodiments of the invention include administering a blood product comprising plasma components from an individual (the "donor individual", or "donor") to an individual suffering from a postoperative condition (the "recipient individual" or "recipient"). By a "blood product comprising plasma components," it is meant any product derived from blood that comprises plasma (e.g. whole blood, blood plasma, or fractions thereof). The term "plasma" is used in its conventional sense to refer to the straw-colored/pale-yellow liquid component of blood composed of about 92% water, 7% proteins such as albumin, gamma globulin, anti-hemophilic factor, and other clotting factors, and 1% mineral salts, sugars, fats, hormones and vitamins. Non-limiting examples of plasma-comprising blood products suitable for use in the subject methods include whole blood treated with anticoagulant (e.g., EDTA, citrate, oxalate, heparin, etc.), blood products produced by filtering whole blood to remove white blood cells ("leukoreduction"), blood products consisting of plasmapheretically-derived or apheretically-derived plasma, fresh-frozen plasma, blood products consisting essentially of purified plasma, and blood products consisting essentially of plasma fractions. In some instances, plasma product that is employed is a non-whole blood plasma product, by which is meant that the product is not whole blood, such that it lacks one or more components found in whole blood, such as erythrocytes, leukocytes, etc., at least to the extent that these components are present in whole blood. In some instances, the plasma product is substantially, if not completely, acellular, where in such instances the cellular content may be 5% by volume or less, such as 1% or less, including 0.5% or less, where in some instances acellular plasma fractions are those compositions that completely lack cells, i.e., they include no cells.

Collection of blood products comprising plasma components. Embodiments of the methods described herein include administration of blood products comprising plasma components which can be derived from donors, including human volunteers. The term, "human-derived" can refer to such products. Methods of collection of plasma comprising blood products from donors are well-known in the art. (See, e.g., AABB TECHNICAL MANUAL, (Mark A. Fung, et al., eds., 18th ed. 2014), herein incorporated by reference).

In one embodiment, donations are obtained by venipuncture. In another embodiment, the venipuncture is only a single venipuncture. In another embodiment, no saline volume replacement is employed. In a preferred embodiment, the process of plasmapheresis is used to obtain the plasma comprising blood products. Plasmapheresis can comprise the removal of a weight-adjusted volume of plasma with the return of cellular components to the donor. In the preferred embodiment, sodium citrate is used during plasmapheresis in order to prevent cell clotting. The volume of plasma collected from a donor is preferably between 690 to 880 mL after citrate administration, and preferably coordinates with the donor's weight.

C. Plasma Fractions

During the Second World War, there arose a need for a stable plasma expander which could be employed in the battlefield when soldiers lost large amounts of blood. As a result, methods of preparing freeze-dried plasma were developed. However, use of freeze-dried plasma was difficult in combat situations since reconstitution required sterile water. As an alternative, Dr. E. J. Cohn suggested that albumin could be used, and prepared a ready-to-use stable solution that could be introduced immediately for treatment of shock. (See Johan, Current Approaches to the Preparation of Plasma Fractions in (Biotechnology of Blood) 165 (Jack Goldstein ed., 1st ed. 1991)). Dr. Cohn's procedure of purifying plasma fractions utilized cold ethanol for its denaturing effect and employs changes in pH and temperature to achieve separation.

An embodiment of the methods described herein includes the administration of plasma fractions to a subject. Fractionation is the process by which certain protein subsets are separated from plasma. Fractionation technology is known in the art and relies on steps developed by Cohn et al. during the 1940s. (E. Cohn, Preparation and properties of serum and plasma proteins. IV. A system for the separation into fractions of the protein and lipoprotein components of biological tissues and fluids. 68 J Am Chem Soc 459 (1946), herein incorporated by reference). Several steps are involved in this process, each step involving specific ethanol concentrations as well as pH, temperature, and osmolality shifts which result in selective protein precipitation. Precipitates are also separated via centrifugation or precipitation. The original "Cohn fractionation process" involved separation of proteins through precipitates into five fractions, designated fraction I, fraction II+III, fraction IV-1, fraction IV-4 and fraction V. Albumin was the originally identified endpoint (fraction V) product of this process. In accordance with embodiments of the invention, each fraction (or effluent from a prior separation step) contains or potentially contains therapeutically-useful protein fractions. (See Thierry Burnouf, Modern Plasma Fractionation, 21(2) Transfusion Medicine Reviews 101 (2007); Adil Denizli, Plasma fractionation: conventional and chromatographic methods for albumin purification, 4 J. Biol. & Chem. 315, (2011); and T. Brodniewicz-Proba, Human Plasma Fractionation and the Impact of New Technologies on the Use and Quality of Plasma-derived Products, 5 Blood Reviews 245 (1991), and U.S. Pat. Nos. 3,869,431, 5,110,907, 5,219,995, 7,531,513, and 8,772,461 which are herein incorporated by reference). Adjustment of the above experimental parameters can be made in order to obtain specific protein fractions.

More recently, fractionation has reached further complexity, and as such, comprises additional embodiments of the invention. This recent increase in complexity has occurred through: the introduction of chromatography resulting in isolation of new proteins from existing fractions like cryoprecipitate, cryo-poor plasma, and Cohn fractions; increasing IgG recovery by integrating chromatography and the ethanol fractionation process; and viral reduction/inactivation/removal. (Id.) In order to capture proteins at physiological pH and ionic strength, anion-exchange chromatography can be utilized. This preserves functional activity of proteins and/or protein fractions. Heparin and monoclonal antibodies are also used in affinity chromatography. Additionally, fractionation using gel filtration, fraction by salt, and fractionation by polyethylene glycol are used. (Hosseini M *Iran J Biotech,* 14(4): 213-20 (2016) herein incorporated by reference). One of ordinary skill in the art would recognize that the parameters and techniques described above may be adjusted to obtain specifically-desired plasma protein-containing fractions.

Blood plasma fractionation can also be ammonium sulfate-based. (See, e.g., Odunuga O O, *Biochem Compounds,* 1:3 (2013); Wingfield P T, *Curr Protoc Protein Sci*, Appx. 3 (2001), herein incorporated by reference). In addition to obtaining specific blood fractions, ammonium sulfate-based fractionation has been employed to reduce abundant proteins from plasma. (Saha S, et al., *J. Proteomics Bioinform,* 5(8) (2012), herein incorporated by reference).

In an embodiment of the invention, blood plasma is fractionated in an industrial setting. Frozen plasma is thawed at 1° C. to 4° C. Continuous refrigerated centrifugation is applied to the thawed plasma and cryoprecipitate isolated. Recovered cryoprecipitate is frozen at −30° C. or lower and stored. The cryoprecipitate-poor ("cryo-poor") plasma is immediately processed for capture (via, for example, primary chromatography) of labile coagulation factors such as factor IX complex and its components as well as protease inhibitors such as antithrombin and C1 esterase inhibitor. Serial centrifugation and precipitate isolation can be applied in subsequent steps. Such techniques are known to one of ordinary skill in the art and are described, for example, in U.S. Pat. Nos. 462,480, 5,219,995, 5,288,853, and U.S. patent application nos. 20140343255 and 20150343025, which disclosures are incorporated by reference in their entirety herein.

In an embodiment of the invention, the plasma fraction may comprise a plasma fraction containing a substantial concentration of albumin. In another embodiment of the invention, the plasma fraction may comprise a plasma fraction containing a substantial concentration of IgG or intravenous immune globulin (IGIV) (e.g. Gamunex-C®). In another embodiment of the invention the plasma fraction may comprise an IGIV plasma fraction, such as Gamunex-C® which has been substantially depleted of immune globulin (IgG) by methods well-known by one of ordinary skill in the art, such as for example, Protein A-mediated depletion. (See Keshishian, H., et al., Multiplexed, Quantitative Workflow for Sensitive Biomarker Discovery in Plasma Yields Novel Candidates for Early Myocardial Injury, Molecular & Cellular Proteomics, 14 at 2375-93 (2015)). In an additional embodiment, the blood plasma fraction may be one in which substantially all the clotting factors are removed in order to retain the efficacy of the fraction with reduced risk of thromboses. For example, the plasma fraction may be a plasma fraction as described in U.S. Patent No. 62/376,529 filed on Aug. 18, 2016; the disclosure of which is incorporated by reference in its entirety herein.

D. Albumin Products

To those having ordinary skill in the art, there are two general categories of Albumin Plasma Products ("APP"): plasma protein fraction ("PPF") and human albumin solution ("HAS"). PPF is derived from a process with a higher yield than HAS but has a lower minimum albumin purity than HAS (>83% for PPF and >95% for HAS). (Production of human albumin solution: a continually developing colloid, P. Matejtschuk et al., British J. of Anaesthesia 85(6):

887-95, at 888 (2000)). In some instances, PPF has albumin purity of between 83% and 95% or alternatively 83% and 96%. The albumin purity can be determined by electrophoresis or other quantifying assays such as, for example, by mass spectrometry. Additionally, some have noted that PPF has a disadvantage because of the presence of protein "contaminants" such as PKA. Id. As a consequence, PPF preparations have lost popularity as Albumin Plasma Products, and have even been delisted from certain countries' Pharmacopoeias. Id. Contrary to these concerns, the invention makes beneficial use of these "contaminants." Besides α, β, and γ globulins, as well as the aforementioned PKA, the methods of the invention utilize additional proteins or other factors within the "contaminants" that promote processes such as neurogenesis, neuronal cell survival, improved cognition or motor function and decreased neuroinflammation.

Those of skill in the art will recognize that there are, or have been, several commercial sources of PPF (the "Commercial PPF Preparations.") These include Plasma-Plex™ (Armour Pharmaceutical Co., Tarrytown, NY), Plasmanate™ PPF (Grifols, Clayton, NC), Plasmatein™ (Alpha Therapeutics, Los Angeles, CA), and Protenate™ PPF (Baxter Labs, Inc. Deerfield, IL). Those of skill in the art will also recognize that there are, or have been, several commercial sources of HAS (the "Commercial HAS Preparations.") These include Albuminar™ (CSL Behring), AlbuRx™ (CSL Behring), Albutein™ (Grifols, Clayton, NC), Buminate™ (Baxatla, Inc., Bannockburn, IL), Flexbumin™ (Baxalta, Inc., Bannockburn, IL), and Plasbumin™ (Grifols, Clayton, NC).

1. Plasma Protein Fraction (Human) (PPF)

According to the United States Food and Drug Administration ("FDA"), "Plasma Protein Fraction (Human)," or PPF, is the proper name of the product defined as "a sterile solution of protein composed of albumin and globulin, derived from human plasma." (Code of Federal Regulations "CFR" 21 CFR 640.90 which is herein incorporated by reference). PPF' s source material is plasma recovered from Whole Blood prepared as prescribed in 21 CFR 640.1-640.5 (incorporated by reference herein), or Source Plasma prepared as prescribed in 21 CFR 640.60-640.76 (incorporated by reference herein).

PPF is tested to determine it meets the following standards as per 21 CFR 640.92 (incorporated by reference herein):

(a) The final product shall be a 5.0 +/−0.30 percent solution of protein; and (b) The total protein in the final product shall consist of at least 83 percent albumin, and no more than 17 percent globulins. No more than 1 percent of the total protein shall be gamma globulin. The protein composition is determined by a method that has been approved for each manufacturer by the Director, Center for Biologics Evaluation and Research, Food and Drug Administration.

As used herein, "Plasma Protein Fraction" or "PPF" refers to a sterile solution of protein composed of albumin and globulin, derived from human plasma, with an albumin content of at least 83% with no more than 17% globulins (including α1, α2, β, and γ globulins) and other plasma proteins, and no more than 1% gamma globulin as determined by electrophoresis. (Hink, J. H., Jr., et al., Preparation and Properties of a Heat-Treated Human Plasma Protein Fraction, VOX SANGUINIS 2(174) (1957)). PPF can also refer to a solid form, which when suspended in solvent, has similar composition. The total globulin fraction can be determined through subtracting the albumin from the total protein. (Busher, J., Serum Albumin and Globulin, CLINICAL METHODS: THE HISTORY, PHYSICAL, AND LABORATORY EXAMINATIONS, Chapter 10, Walker H K, Hall W D, Hurst J D, eds. (1990)).

2. Albumin (Human) (HAS)

According to the FDA, "Albumin (Human)" (also referred to herein as "HAS") is the proper name of the product defined as "sterile solution of the albumin derived from human plasma." (Code of Federal Regulations "CFR" 21 CFR 640.80 which is herein incorporated by reference.) The source material for Albumin (Human) is plasma recovered from Whole Blood prepared as prescribed in 21 CFR 640.1-640.5 (incorporated by reference herein), or Source Plasma prepared as prescribed in 21 CFR 640.60-640.76 (incorporated by reference herein). Other requirements for Albumin (Human) are listed in 21 CFR 640.80-640.84 (incorporated by reference herein).

Albumin (Human) is tested to determine if it meets the following standards as per 21 CFR 640.82:

(a) Protein concentration. Final product shall conform to one of the following concentrations: 4.0 +/−0.25 percent; 5.0 +/−0.30 percent; 20.0 +/−1.2 percent; and 25.0 +/−1.5 percent solution of protein.

(b) Protein composition. At least 96 percent of the total protein in the final product shall be albumin, as determined by a method that has been approved for each manufacturer by the Director, Center for Biologics Evaluation and Research, Food and Drug Administration.

As used herein, "Albumin (Human)" or "HAS" refers to a to a sterile solution of protein composed of albumin and globulin, derived from human plasma, with an albumin content of at least 95%, with no more than 5% globulins (including α1, α2, β, and γ globulins) and other plasma proteins. HAS can also refer to a solid form, which when suspended in solvent, has similar composition. The total globulin fraction can be determined through subtracting the albumin from the total protein.

As can be recognized by one having ordinary skill in the art, PPF and HAS fractions can also be freeze-dried or in other solid form. Such preparations, with appropriate additives, can be used to make tablets, powders, granules, or capsules, for example. The solid form can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

E. Clotting Factor-Reduced Fractions

Another embodiment of the invention uses a blood plasma fraction from which substantially all of the clotting factors are removed in order to retain the efficacy of the fraction with reduced risk of thromboses. Conveniently, the blood product can be derived from a young donor or pool of young donors and can be rendered devoid of IgM in order to provide a young blood product that is ABO compatible. Currently, plasma that is transfused is matched for ABO blood type, as the presence of naturally occurring antibodies to the A and B antigens can result in transfusion reactions. IgM appears to be responsible for transfusion reactions when patients are given plasma that is not ABO matched. Removal of IgM from blood products or fractions helps eliminate transfusion reactions in subjects who are administered the blood products and blood plasma fractions of the invention.

Accordingly, in one embodiment, the invention is directed to a method of treating a subject suffering from an unwanted condition associated with postoperative recovery. The method comprises: administering to the subject a blood product or blood fraction derived from whole-blood from an individual or pool of individuals, wherein the blood product or blood fraction is substantially devoid of (a) at least one clotting factor and/or (b) IgM. In some embodiments, the individual(s) from whom the blood product or blood fraction is derived are young individuals. In some embodiments, the blood product is substantially devoid of at least one clotting factor and IgM. In certain embodiments, the blood product is substantially devoid of fibrinogen (Factor I). In additional embodiments, the blood product substantially lacks erythrocytes and/or leukocytes. In further embodiments, the blood product is substantially acellular. In other embodiments, the blood product is derived from plasma. Such embodiments of the invention are further supported by U.S. Patent Application No. 62/376,529 filed on Aug. 18, 2016, which is incorporated by reference in its entirety herein.

F. Protein-Enriched Plasma Protein Products Treatment

Additional embodiments of the invention use plasma fractions with reduced albumin concentration compared to PPF, but with increased amounts of globulins and other plasma proteins (what have been referred to by some as "contaminants"). The embodiments, as with PPF, HAS, Effluent I, and Effluent II/III are all effectively devoid of clotting factors. Such plasma fractions are hereinafter referred to as "protein-enriched plasma protein products." For example, an embodiment of the invention may use a protein-enriched plasma protein product comprised of 82% albumin and 18% α, β, and γ globulins and other plasma proteins. Another embodiment of the invention may use a protein-enriched plasma protein product comprised of 81% albumin and 19% of α, β, and γ globulins and/or other plasma proteins. Another embodiment of the invention may use a protein-enriched plasma protein product comprised of 80% albumin and 20% of α, β, and γ globulins and/or other plasma proteins. Additional embodiments of the invention may use protein-enriched plasma protein products comprised of 70-79% albumin and a corresponding 21-30% of α, β, and γ globulins and other plasma proteins. Additional embodiments of the invention may use protein-enriched plasma protein products comprised of 60-69% albumin and a corresponding 31-40% of α, β, and γ globulins and other plasma proteins. Additional embodiments of the invention may use protein-enriched plasma protein products comprised of 50-59% albumin and a corresponding 41-50% of α, β, and γ globulins and other plasma proteins. Additional embodiments of the invention may use protein-enriched plasma protein products comprised of 40-49% albumin and a corresponding 51-60% of α, β, and γ globulins and other plasma proteins. Additional embodiments of the invention may use protein-enriched plasma protein products comprised of 30-39% albumin and a corresponding 61-70% of α, β, and γ globulins and other plasma proteins. Additional embodiments of the invention may use protein-enriched plasma protein products comprised of 20-29% albumin and a corresponding 71-80% of α, β, and γ globulins and other plasma proteins. Additional embodiments of the invention may use protein-enriched plasma protein products comprised of 10-19% albumin and a corresponding 81-90% of α, β, and γ globulins and other plasma proteins. Additional embodiments of the invention may use protein-enriched plasma protein products comprised of 1-9% albumin and a corresponding 91-99% of α, β, and γ globulins and other plasma proteins. A further embodiment of the invention may use protein-enriched plasma protein products comprised of 0% albumin and 100% of α, β, and γ globulins and other plasma proteins Embodiments of the invention described above may also have total gamma globulin concentrations of 1-5%.

The specific concentrations of proteins in a plasma fraction may be determined using techniques well-known to a person having ordinary skill in the relevant art. By way of example, and not limitation, such techniques include electrophoresis, mass spectrometry, ELISA analysis, and Western blot analysis.

G. Preparation of Plasma Fractions

Methods of preparing PPF and other plasma fractions are well-known to those having ordinary skill in the art. An embodiment of the invention allows for blood used in the preparation of human plasma protein fraction to be collected in flasks with citrate or anticoagulant citrate dextrose solution (or other anticoagulant) for inhibition of coagulation, with further separation of Fractions I, II+III, IV, and PPF as per the method disclosed in Hink et al. (See Hink, J. H., Jr., et al., Preparation and Properties of a Heat-Treated Human Plasma Protein Fraction, VOX SANGUINIS 2(174) (1957), herein incorporated by reference.) According to this method, the mixture can be collected to 2-8° C. The plasma can then subsequently be separated by centrifugation at 7° C., removed, and stored at −20° C. The plasma can then be thawed at 37° C. and fractionated, preferably within eight hours after removal from −20° C. storage.

Plasma can be separated from Fraction I using 8% ethanol at pH 7.2 and a temperature at −2 to −2.5° C. with protein concentration of 5.1 to 5.6 percent. Cold 53.3 percent ethanol (176 mL/L of plasma) with acetate buffer (200 mL 4 M sodium acetate, 230 mL glacial acetic acid quantum satis to 1 L with $H_2O$) can be added using jets at a rate, for example, of 450 mL/minute during the lowering the plasma temperature to −2° C. Fraction I can be separated and removed from the effluent (Effluent I) through ultracentrifugation. Fibrinogen can be obtained from Fraction I as per methods well-known to those having ordinary skill in the art.

Fraction II+III can be separated from Effluent I through adjustment of the effluent to 21 percent ethanol at pH 6.8, temperature at −6° C., with protein concentration of 4.3 percent. Cold 95 percent ethanol (176 mL/L of Effluent I) with 10 M acetic acid used for pH adjustment can be added using jets at a rate, for example, of 500 mL/minute during the lowering of the temperature of Effluent I to −6° C. The resulting precipitate (Fraction II+III) can be removed by centrifugation at −6° C. Gamma globulin can be obtained from Fraction II+III using methods well-known to those having ordinary skill in the art.

Fraction IV-1 can be separated from Effluent II+III ("Effluent II/III") through adjustment of the effluent to 19 percent ethanol at pH 5.2, temperature at −6° C., and protein concentration of 3 percent. $H_2O$ and 10 M acetic acid used for pH adjustment can be added using jets while maintaining Effluent II/III at −6° C. for 6 hours. Precipitated Fraction VI-1 can be settled at −6° C. for 6 hours and subsequently separated from the effluent by centrifugation at the same temperature. Stable plasma protein fraction can be recovered from Effluent IV-1 through adjustment of the ethanol concentration to 30 percent at pH 4.65, temperature −7° C. and protein concentration of 2.5 percent. This can be accomplished by adjusting the pH of Effluent IV-1 with cold acid-alcohol (two parts 2 M acetic acid and one-part 95 percent ethanol). While maintaining a temperature of −7° C., to every liter of adjusted Effluent IV-1 170 mL cold ethanol (95%) is added. Proteins that precipitate can be allowed to settle for 36 hours and subsequently removed by centrifugation at −7° C.

The recovered proteins (stable plasma protein fraction) can be dried (e.g. by freeze drying) to remove alcohol and $H_2O$. The resulting dried powder can be dissolved in sterile distilled water, for example using 15 liters of water/kg of powder, with the solution adjusted to pH 7.0 with 1 M NaOH. A final concentration of 5 percent protein can be achieved by adding sterile distilled water containing sodium acetyl tryptophanate, sodium caprylate, and NaCl, adjusting to final concentrations of 0.004 M acetyl tryptophanate, 0.004 M caprylate, and 0.112 M sodium. Finally, the solution can be filtered at 10° C. to obtain a clear solution and subsequently heat-treated for inactivation of pathogens at 60° C. for at least 10 hours.

One having ordinary skill in the art would recognize that each of the different fractions and effluents described above could be used with the methods of the invention to treat conditions associated with postoperative recovery. For example, and not by way of limitation, Effluents I or Effluent II/III may be utilized to treat conditions associated with postoperative recovery or to accelerate postoperative recovery and are embodiments of the invention.

The preceding methods of preparing plasma fractions and plasma protein fraction (PPF) are only exemplary and involve merely embodiments of the invention. One having ordinary skill in the art would recognize that these methods can vary. For example, pH, temperature, and ethanol concentration, among other things can be adjusted to produce different variations of plasma fractions and plasma protein fraction in the different embodiments and methods of the invention. In another example, additional embodiments of the invention contemplate the use of nanofiltration for the removal/inactivation of pathogens from plasma fractions and plasma protein fraction.

An additional embodiment of the invention contemplates methods and composition using and/or comprising additional plasma fractions. For example, the invention, among other things, contemplates that specific concentrations of albumin are not critical for treating conditions associated with postoperative recovery or for accelerating postoperative recovery. Hence, fractions with reduced albumin concentration, such as those fractions having below 83% albumin, are contemplated by the invention.

H. Treatment

Aspects of the methods of the inventions described herein include treatment of a subject with a plasma comprising blood product, such as a blood plasma fraction, e.g., as described above. An embodiment includes treatment of a human subject with a plasma comprising blood product. One of skill in the art would recognize that methods of treatment of subjects with plasma comprising blood products are recognized in the art. By way of example, and not limitation, one embodiment of the methods of the inventions described herein is comprised of administering fresh frozen plasma to a subject for treatment of conditions associated with postoperative recovery. In one embodiment, the plasma comprising blood product is administered immediately, e.g., within about 12-48 hours of collection from a donor, to the individual suffering from a condition associated with postoperative recovery. In such instances, the product may be stored under refrigeration, e.g., 0-10° C. In another embodiment, fresh frozen plasma is one that has been stored frozen (cryopreserved) at −18° C. or colder. Prior to administration, the fresh frozen plasma is thawed and once thawed, administered to a subject 60-75 minutes after the thawing process has begun. Each subject preferably receives a single unit of fresh frozen plasma (200-250 mL), the fresh frozen plasma preferably derived from donors of a pre-determined age range. In one embodiment of the invention, the fresh frozen plasma is donated by (derived from) young individuals. In another embodiment of the invention, the fresh frozen plasma is donated by (derived from) donors of the same gender. In another embodiment of the invention, the fresh frozen plasma is donated by (derived from) donors of the age range between 18-22 years old.

In an embodiment of the invention the compositions of the invention the compositions (e.g. plasma comprising blood product, such as a blood plasma fraction) are administered intravenously. The compositions of the invention may also be delivered intraperitoneally. In another embodiment of the invention, the compositions of the invention may be delivered per os, subcutaneously, or topically. Topical formulations for treating wounds and promoting would healing as known in the art as gels, creams, ointments, gauze, patches and the like, and the compositions of the invention may be formulated as such. (See, e.g., Kahn A W, et al., *Pharmacogn Mag,* 9(Suppl 1):S6-S10 (2013); U.S. Pat. Nos. 5,641,483; 4,885,163; 8,313,764, which are incorporated herein in their entirety).

In an embodiment of the invention, the plasma comprising blood products are screened after donation by blood type. In another embodiment of the invention, the plasma comprising blood products are screened for infectious disease agents such as HIV I & II, HBV, HCV, HTLV I & II, anti-HBc per the requirements of 21 CFR 640.33 and recommendations contained in FDA guidance documents.

In yet another embodiment of the invention, the subject is treated with a Plasma Fraction. In an embodiment of the invention, the plasma fraction is a PPF or a HAS. In a further embodiment of the invention, the plasma fraction is one of the Commercial PPF Preparations of the Commercial HAS Preparations. In another embodiment of the invention the plasma fraction is a PPF or HAS derived from a pool of individuals of a specific age range, such as young individuals, or is a modified PPF or HAS fraction which has been subjected to additional fractionation or processing (e.g. PPF or HAS with one or more specific proteins partially or substantially removed). In another embodiment of the invention, the plasma fraction is an IGIV plasma fraction which has been substantially depleted of immune globulin (IgG). A blood fraction which is "substantially depleted" or which has specific proteins "substantially removed," such as IgG, refers to a blood fraction containing less than about 50% of the amount that occurs in the reference product or whole blood plasma, such as less than 45%, 40%, 35%, 30%, 25%, 20%, 15%, 5%, 4%, 3%, 2%, 1%, 0.5%, 0.25%, 0.1%, undetectable levels, or any integer between these values, as measured using standard assays well known in the art.

I. Administration

Aspects of the methods of the inventions described herein include treatment of a subject with a plasma comprising blood product, such as a blood plasma or Plasma Fraction, e.g., as described above. An embodiment includes treatment of a human subject with a plasma comprising blood product. One of skill in the art would recognize that methods of treatment of subjects with plasma comprising blood products are recognized in the art. By way of example, and not limitation, one embodiment of the methods of the inventions described herein is comprised of administering fresh frozen plasma to a subject for treatment of conditions associated with postoperative recovery. In one embodiment, the plasma comprising blood product is administered immediately, e.g., within about 12-48 hours of collection from a donor, to the individual suffering from an unwanted condition associated with postoperative recovery. In such instances, the product may be stored under refrigeration, e.g., 0-10° C. In another embodiment, fresh frozen plasma is one that has been stored frozen (cryopreserved) at −18° C. or colder. Prior to administration, the fresh frozen plasma is thawed and once thawed, administered to a subject 60-75 minutes after the thawing process has begun. Each subject preferably receives a single unit of fresh frozen plasma (200-250 mL), the fresh frozen plasma preferably derived from donors of a pre-determined age range. In one embodiment of the invention, the fresh frozen plasma is donated by (derived from) young individuals. In another embodiment of the invention, the fresh frozen plasma is donated by (derived from) donors of the same gender. In another embodiment of the invention, the fresh frozen plasma is donated by (derived from) donors of the age range between 18-22 years old.

In an embodiment of the invention, the plasma comprising blood products are screened after donation by blood type. In another embodiment of the invention, the plasma comprising blood products are screened for infectious disease agents such as HIV I & II, HBV, HCV, HTLV I & II, anti-HBc per the requirements of 21 CFR 640.33 and recommendations contained in FDA guidance documents.

In yet another embodiment of the invention, the subject is treated with a Plasma Fraction. In an embodiment of the invention, the plasma fraction is PPF or HAS. In a further embodiment of the invention, the plasma fraction is one of the Commercial PPF Preparations or the Commercial HAS Preparations. In another embodiment of the invention the plasma fraction is a PPF or HAS derived from a pool of individuals of a specific age range, such as young individuals, or is a modified PPF or HAS fraction which has been subjected to additional fractionation or processing (e.g. PPF or HAS with one or more specific proteins partially or substantially removed). In another embodiment of the invention, the plasma fraction is an IGIV plasma fraction which has been substantially depleted of immune globulin (IgG). A blood fraction which is "substantially depleted" or which has specific proteins "substantially removed," such as IgG, refers to a blood fraction containing less than about 50% of the amount that occurs in the reference product or whole blood plasma, such as less than 45%, 40%, 35%, 30%, 25%, 20%, 15%, 5%, 4%, 3%, 2%, 1%, 0.5%, 0.25%, 0.1%, undetectable levels, or any integer between these values, as measured using standard assays well known in the art.

An embodiment of the invention includes treating a subject suffering from a condition associated with postoperative recovery by administering to the subject an effective amount of blood plasma or Plasma Fraction. Another embodiment of the invention includes administering the effective amount of blood plasma or Plasma Fraction and subsequently monitoring the subject for improved function, wound healing, the presence of markers, decreased pain, or decreased inflammation. Another embodiment of the invention includes treating a subject suffering from a condition associated with postoperative recovery by administering to the subject an effective amount of blood plasma or Plasma Fraction wherein the blood plasma or Plasma Fraction is administered in a manner resulting in improved function wound healing, the presence of markers, decreased pain, or decreased inflammation after the mean or median half-life of the blood plasma proteins or Plasma Fraction proteins been reached, relative to the most recent administered dose (referred to as "Pulsed Dosing" or "Pulse Dosed" herein) (See U.S. Pat. No. 10,357,513 and U.S. patent application Ser. No. 15/961,618 and Ser. No. 62/701,411, which are herein incorporated by reference in their entirety). Another embodiment of the invention includes administering the blood plasma or Plasma Fraction via a dosing regimen of at least two consecutive days and monitoring the subject for improved function or HSC marker levels at least 3 days after the date of last administration. A further embodiment of the invention includes administering the blood plasma or Plasma Fraction via a dosing regimen of at least 3, 4, 5, 6, 7, 8, 9, 10, 11, 12, 13, or 14 consecutive days and monitoring the subject for improved function, wound healing, the presence of markers, decreased pain, or decreased inflammation at least 3 days after the date of last administration. Yet another embodiment of the invention includes administering the blood plasma or Plasma Fraction via a dosing regimen of at least 2 consecutive days and after the date of last administration, monitoring for functional improvement, wound healing, the presence of markers, decreased pain, or decreased inflammation beyond when the average half-life of the proteins in the blood plasma or Plasma Fraction has been reached. Another embodiment of the invention includes administering the blood plasma or Plasma Fraction via a dosing regimen of 2 to 14 non-consecutive days wherein each gap between doses may be between 0-3 days each.

In some instances, Pulsed Dosing in accordance with the invention includes administration of a first set of doses, e.g., as described above, followed by a period of no dosing, e.g., a "dosing-free period", which in turn is followed by administration of another dose or set of doses. The duration of this "dosing-free" period, may vary, but in some embodiments, is 7 days or longer, such as 10 days or longer, including 14 days or longer, wherein some instances the dosing-free period ranges from 15 to 365 days, such as 30 to 90 days and including 30 to 60 days. As such, embodiments of the methods include non-chronic (i.e., non-continuous) dosing, e.g., non-chronic administration of a blood plasma product. In some embodiments, the pattern of Pulsed Dosing followed by a dosing-free period is repeated for a number of times, as desired, where in some instances this pattern is continued for 1 year or longer, such as 2 years or longer, up to and including the life of the subject. Another embodiment of the invention includes administering the blood plasma or Plasma Fraction via a dosing regimen of 5 consecutive days, with a dosing-free period of 2-3 days, followed by administration for 2-14 consecutive days.

Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances, reverse unwanted conditions associated with postoperative recovery.

J. Plasma Protein Fraction

In practicing methods of the invention, a plasma fraction is administered to the subject. In an embodiment, the plasma fraction is plasma protein fraction (PPF). In additional embodiments, the PPF is selected from the Commercial PPF Preparations.

In another embodiment, the PPF is comprised of 88% normal human albumin, 12% alpha and beta globulins and not more than 1% gamma globulin as determined by electrophoresis. Further embodiments of this embodiment used in practicing methods of the invention include, for example, the embodiment as a 5% solution of PPF buffered with sodium carbonate and stabilized with 0.004 M sodium caprylate and 0.004 M acetyltryptophan. Additional formulations, including those modifying the percentage of PPF (e.g. about 1% to about 10%, about 10% to about 20%, about 20% to 25%, about 25% to 30%) in solution as well as the concentrations of solvent and stabilizers may be utilized in practicing methods of the invention.

K. Plasma Fractions of Specific Donor Age

Additional embodiments of the invention include administering a plasma protein fraction derived from the plasma of individuals of certain age ranges. An embodiment includes administering PPF or HAS which have been derived from the plasma of young individuals. In another embodiment of the invention the young individuals are of a single specific age or a specific age range. In yet another embodiment, the average age of the donors is less than that of the subject or less than the average age of the subjects being treated.

Certain embodiments of the invention include pooling blood or blood plasma from individuals of specific age ranges and fractionating the blood plasma as described above to attain a plasma protein fraction product such as PPF or HAS. In an alternate embodiment of the invention, the plasma protein fraction or specific plasma protein fraction is attained from specific individuals fitting a specified age range.

L. Indications

The subject methods and plasma-comprising blood products and fractions find use in treating unwanted conditions associated with postoperative recovery and even accelerating postoperative recovery. Such conditions and indications include, by way of example and not limitation, pain and wound healing. The subject methods and compositions of the invention also find use in treating acute and chronic pain in diseases or conditions not necessarily related to postoperative recovery. The subject methods and compositions also find use in treating wound healing that is not necessarily associated with postoperative recovery. The subject methods and compositions also find use in promoting or stimulating remyelination and treating diseases related to myelination such as multiple sclerosis.

The subject methods and plasma-comprising blood products and fractions also find use in treating indications associated with the nervous system. Such conditions, by way of example and not limitation, include central nervous system conditions such as central neuropathic pain, spinal cord injury, myelopathy, and central neuropathic pain associated with postoperative recovery. Seventeen thousand new cases of spinal injury occur per year with a prevalence of about 300,000, of which 40-75% of subjects with spinal injury having central neuropathic pain. (Jadad A et al., *AHRQ Evidence Report Summaries*, Agency for Healthcare Research and Quality; (1998-2005); https://www.nscisc.uab.edu/Public/Facts%202016.pdf; and https://www.nscisc.uab.edu/PublicDocuments/fact figures docs/Facts%202012%20Feb%20Fina 1.pdf). One-third of patients experience intense pain with only ⅓ having a 50% or greater reduction in pain with treatment. (Charbonneau R, *CMAJ,* 189(2):E48-E49 (2017); and Hadjipavlou G, et al., *BJA Education,* 16(8):264-68 (2016)). Myelopathy has an occurrence rate of 605 per 1,000,000 with surgical options, but no pharmacologic treatments, indicating an unmet need in the field. (Nouri A, et al., *Spine,* 40(12):E675-93 (2015); *The Lancet Neurology*, editorial 18(7):P615 (2019)).

These conditions also include, by way of example and not limitation, plexus/nerve root conditions such as plexopathy, cervical radiculopathy, and sciatica (lumbar radiculopathy). Plexopathy has a 2-3 per 100,000 incidence. Its current options include management of neuropathic pain with anti-epileptics and antidepressants, indicating an unmet need. Cervical radiculopathy's incidence is 100 per 100,000 males and 60 per 100,000 females. (McCartney S, et al., *Br. J. Gen. Pract.,* 68(666):44-46 (2018)). Sciatica has an annual incidence of 1-5% and although many cases resolve spontaneously, sciatica becomes less responsive to treatment with prolonged duration of episodes. Treatments options include surgical procedures, standard pain medications, and steroids, indicating a need for new therapies. (Lewis R, et al., *Health Technology Assessment—The Clinical Effectiveness and Cost—Effectiveness of Management Strategies for Sciatica: Systematic Review and Economic Model*, No. 15.39 NIHR Journals Library (2011)).

Additional indications include peripheral nervous system disorders. These include, by way of example and not limitation: peripheral neuropathy; peripheral neuropathy associated with post-operative recovery; carpal tunnel syndrome; chemotherapy-induced peripheral neuropathy; compression and trauma; diabetic neuropathy; peripheral neuropathy associated with shingles (postherpetic neuralgia); complex regional pain syndrome; and trigeminal neuralgia. Peripheral neuropathy is a disorder of the peripheral nerves and affects at least 20 million people in the United States along. Almost 60 percent of subjects with diabetes experience diabetic neuropathy, a type of peripheral neuropathy. (http://www.healthcommunities.com/neuropathy/overview-of-neuropathy.shtml). Carpal tunnel syndrome affects 3-6% of adults, and treatments include splints, steroids, and surgery. (LeBlanc K E, et al., *Am Fam Physician,* 83(8):952-58 (2011)). Chemotherapy-induced peripheral neuropathy occurs in 40-60% of patients both during and up to 3 months after receiving chemotherapy, with 650,000 patients reported to receive chemotherapy per year. Peripheral neuropathy leads to dose reductions in chemotherapy or even discontinuation, impacting quality of life, with no medication or supplement having been shown to prevent the disorder. (JAMA Oncology, 5(5):750, (2019)). Peripheral neuropathy related to compression and trauma occurs in 2-3% of trauma patients, with 3 million cases of trauma occurring in the United States. Although surgery is often effective, there is a need for new pharmacological agents. (*American Association for the Surgery of Trauma—Trauma Facts*, available at http://www.aast.org/trauma-facts; and Novak C B, *Medscape—Peripheral Nerve Injuries*, (Oct. 5, 2018) available at https://emedicine.medscape.com/article/1270360-overview).

Further peripheral nervous system indications that the subject methods and plasma-comprising blood products and fractions also find use in treating include diabetic neuropathy. In the United States, the population of diabetes patients is about 30 million, and 8-26% of those patients suffer from neuropathy. (Risson V, et al., *Incidence and prevalence of painful diabetic neuropathy and postherpetic neuralgia in major* 5 *European countries, the United States and Japan*, Value in Health (20):A339-A811 PSY18 (2017), available at https://www.valueinhealthjournal.com/article/S1098-3015(17)31179-8/pdf). The FDA-approved options for diabetic neuropathic pain include pregabalin, duloxetine, fluoxetine, and tapentadol, all of which many patients do not respond to and none of which directly addresses nerve damage.

Peripheral neuropathy associated with shingles (postherpetic neuralgia) may also be treated by the methods and products of the invention. Twenty percent of shingles patients experience postherpetic neuralgia and there are 1 million cases per year in the United States. (See https://emedicine.medscape.com/article/1143066-overview#a6 https://www.cdc.gov/shingles/hcp/clinical-overview.html.) Gabapentin and pregabalin are approved treatments for the condition but the pain is often refractory to treatment. (Sacks G M, *Am J Manag Care* 19(1 Suppl):S207-13 (2013)).

Additional peripheral neuropathic indications such as complex regional pain syndrome and trigeminal neuralgia may be treated with the methods and compositions of the invention. Five and one half to twenty-six cases occur per 100,000 population. It is associated with severe pain and disability and response to treatment is variable, indicating a high unmet need. (*Complex Region Pain Syndrome Fact Sheet*, National Institutes of Health—National Institute of Neurological Disorders and Stroke, available at https://www.ninds.nih.gov/Disorders/Patient-Caregiver-Education/Fact-Sheets/Complex-Regional-Pain-Syndrome-Fact-Sheet). Trigeminal neuralgia occurs in 4.2-28.9 per 100,000 population. It has a significant impact on quality of life, and can become resistant to treatment over time, requiring patients to try many different treatments. (Wu N, et al., *J Pain,* 18(Suppl 4):S69, (2017)). The only approved treatment is carbamazepine. Hence, there is an unmet need to treat the pain experienced by these patients.

Additional indications that may be treated with the methods and compositions of the invention include the following examples: central post stroke pain; central pain in multiple sclerosis; post-traumatic headaches; Dejerine-Roussy syndrome; optic neuritis; mitochondrial optic neuropathies; ischemic optic neuropathy; neuromyelitis optica; hereditary optic neuropathies; alcoholic neuropathy; Guillain-Barré Syndrome; Chronic Inflammatory Demyelinating Polyneuropathy (CIDP); Multifocal Motor Neuropathy (MNN); paraneoplastic autonomic neuropathy; peripheral neuropathy associated with sarcoidosis; peripheral neuropathy associated with rheumatoid arthritis; peripheral neuropathy associated with systemic lupus erythematosus; peripheral neuropathy associated with Sjögren's Syndrome; peripheral neuropathy associated with celiac disease; Bell's palsy; peripheral neuropathy associated with Lyme disease; peripheral neuropathy associated with leprosy; peripheral Neuropathy associated with Hepatitis B; peripheral neuropathy associated with Hepatitis C; peripheral neuropathy associated with HIV/AIDS; peripheral neuropathy associated with amyloidosis; peripheral neuropathy associated with anti-MAG; peripheral neuropathy associated with cryoglobulinemia; peripheral neuropathy associated with POEMS; toxin-Induced peripheral neuropathy; peripheral neuropathy associated with kidney disease; peripheral neuropathy associated with vasculitis; peripheral neuropathy associated with vitamin and nutrition deficiency; Charcot-Marie Tooth Disease (CMT); idiopathic peripheral neuropathy; fibromyalgia; and paraneoplastic peripheral neuropathy.

The subject methods and plasma-comprising blood products and fractions also find use in treating indications associated with wound healing. Wounds may be, for example and not as limitation, abrasions, avulsions, incisions, lacerations, and punctures. Such indications can include both chronic wounds and acute wounds. By way of example, and not limitation, wound indications include: chronic wounds such as diabetic ulcer; pressure ulcer; venous ulcer; arterial ulcer; as well as acute wounds such as surgical wounds; traumatic wounds; and burns. But any type of chronic or acute wound may be treated by the subject methods and compositions of the invention.

Diabetic ulcers affect over 2.2 million people in the United States with a global incidence of 6.4%. (Chun D, et al., *J Clin Med,* 8:748 (2019)). Despite several treatment options such as debridement and medical dressings, many patients endure infection and eventually require amputation, highlighting the need for new remedies, in particular pharmacological remedies.

Pressure ulcers occur at an overall rate of 1.8% of hospital admittees, with the total number of annual cases being in the hundreds of thousands. (Bauer K, et al., *Ostomy Wound Manage,* 62(11):30-38 (2016)). Like diabetic ulcers, treatment options such as debridement and medical dressing exist, but many patients experience infection and the ulcers can lead to mortality.

Venous ulcers occur primarily in the leg and comprise a substantial burden on the elderly and occur in about 1% of populations worldwide. (Nelzen O, *Phlebolymphology,* 15(4) (2008)). Venous ulcers are difficult to heal and have a significant tendency to recur than other chronic ulcers. As with diabetic and pressure ulcers, treatment options such as debridement and medical dressing exist, but their recurrence highlights a need for new treatments, in particularly pharmacological-based treatments. Arterial ulcers occur at a rate of approximately a quarter of the rate of venous ulcers. (Gabriel A, *Vascular Ulcers*, (2018), available at https://emedicine.medscape.com/article/1298345-overview#a6). Treatment options also include debridement and medical dressings, but there is a lack of approved pharmacological agents.

Surgical wounds occur in approximately 1.3 million patients per year. (See MediWound—Innovating Solutions for Wound & Burn Care (2019) at 19 available at http://ir.mediwound.com/static-files/cd547017-d1ed-460e-8cb2-0550b1e18a29). Surgical wounds are cuts or incisions in the skin usually made by a scalpel during surgery but can also result from a drain placed during surgery. Healing of surgical wounds is a critical outcome for surgery. Postoperative wound disruption or separation of the layers of the wound with fascial disruption can be a serious complication. (See *Hospital Harm Improvement Resource—Wound Disruption* (2016), available at https://www.patientsafetyinstitute.ca/en/toolsResources/Hospital-Harm-Measure/Documents/Resource-Library/HHIR%20Wound%20Disruption.pdf). Additionally, healing of surgical wounds takes considerably more time in elderly patients compared to younger individuals. (Gerstein A D, *Dermatol Clin,* 11(4):749-57 (1993).

Traumatic wounds are primarily cuts, lacerations, puncture, or abrasion wounds with damage having been caused to the skin and the underlying tissues. Traumatic wounds are typically classified under three groups: acute wounds; cut wounds, and penetrating wounds. Acute wounds are when the skin is ripped or torn, the wound's appearance is jagged, and usually contain foreign bodies like glass, metal, gravel, sand or dirt. Cut wounds are when a sharp object penetrates the skin and underlying subcutaneous tissues. Penetrating wounds are the deepest of the three types and the most severe. Stab wounds and gunshot wounds are typical examples. (See *Traumatic Wounds* available at https://www.woundcarecenters.org/article/wound-types/traumatic-wounds; and Leaper D J, B M J, 332(7540):532-35 (2006)). Although there are several physical treatment options (e.g. sutures), there remains a need for pharmacological interventions.

The World Health Organization estimates that 180,000 deaths occur every year as a result of burns. And non-fatal burn injuries are a leading cause of morbidity, including prolonged hospitalization. (https://www.who.int/news-room/fact-sheets/detail/burns). Typical treatment includes surgical management and dressings. Pharmacological treatment is focused on analgesia, infection control, sedation, circulating blood volume replacement, anticoagulation, and nutrition. (Green A, et al., *Clinical Pharmacist,* 2:249-54 (2010)). The methods and compositions of the invention can fill an unmet need for pharmacological intervention that promotes healing of the damage to the skin and underlying tissues.

The subject methods and plasma-comprising blood products and fractions can be used to treat conditions and indications associated with postoperative recovery at different time points. For example, and not as a limitation, administration to a subject can be performed: pre-operatively, perioperatively (during the procedure), or post-operatively.

One embodiment of the invention is that the subject methods and plasma-comprising blood products and fractions can be used to treat pain. Such pain, by way of example and not limitation, may include acute or chronic pain. Another embodiment of the invention is that the subject methods and plasma-comprising blood products and fractions can also be used to treat central pain or central neuropathy. Central pain includes neurological conditions caused by damage to or dysfunction of the central nervous system (CNS), including the brain, brainstem, and spinal cord. It may affect a large portion of the body or it can be restricted to specific areas. The pain may be constant or intermittent. The pain may be moderate to severe in intensity. Such pain may also be affected by touch, movement, emotions, and temperature changes. The pain may also have an immediate onset after the causative incident or may be delayed by months or years. (See Central Pain Information Page—National Institute of Neurological Disorders and Stroke, *Central Pain Syndrome Information Page*, available at https://www.ninds.nih.gov/disorders/all-disorders/central-pain-syndrome-information-page; and Colloca L, et al., Nat Rev Dis Primers, 3:17002 (2017)). Further embodiments of the invention include using the subject methods and plasma-comprising blood productions and fractions to treat: spinal cord injury (SCI); myelopathy; plexopathy; cervical radiculopathy; sciatica (lumbar radiculopathy); central post stroke pain; central pain in multiple sclerosis; post-traumatic headaches; Dejerine-Roussy syndrome; optic neuritis; mitochondrial optic neuropathies; ischemic optic neuropathy; neuromyelitis optica; and hereditary optic neuropathies.

Another embodiment of the invention is that the subject methods and plasma-comprising blood products and fractions can also be used to treat peripheral pain or peripheral neuropathy. Peripheral neuropathy can refer to several conditions involving damage to the peripheral nervous system. More than 100 peripheral neuropathies have been identified and depend on what type(s) of nerve(s) is/are damaged including motor nerves, sensory nerves, and autonomic nerves. (See Central Page Information Page—National Institute of Neurological Disorders and Stroke, *Peripheral Neuropathy Fact Sheet*, available at https://www.ninds.nih.gov/Disorders/Patient-Caregiver-Education/Fact-Sheets/Peripheral-Neuropathy-Fact-Sheet; and Colloca L, et al., Nat Rev Dis Primers, 3:17002 (2017)). Further embodiments of the invention include using the subject methods and plasma-comprising blood productions and fractions to treat: carpal tunnel syndrome; chemo-induced peripheral neuropathy; compression and trauma; diabetic neuropathy; peripheral neuropathy associated with Shingles (postherpetic neuralgia); complex regional pain syndrome; trigeminal neuralgia; alcoholic neuropathy; Guillain-Barré Syndrome; Chronic Inflammatory Demyelinating Polyneuropathy (CIDP); Multifocal Motor Neuropathy (MNN); paraneoplastic autonomic neuropathy; peripheral neuropathy associated with sarcoidosis; peripheral neuropathy associated with rheumatoid arthritis; peripheral neuropathy associated with systemic lupus erythematosus; peripheral neuropathy associated with Sjögren's Syndrome; peripheral neuropathy associated with celiac disease; Bell's palsy; peripheral neuropathy associated with Lyme disease; peripheral neuropathy associated with leprosy; peripheral neuropathy associated with Hepatitis B; peripheral neuropathy associated with Hepatitis C; peripheral neuropathy associated with HIV/AIDS; peripheral neuropathy associated with amyloidosis; peripheral neuropathy associated with anti-MAG; peripheral neuropathy associated with cryoglobulinemia; peripheral neuropathy associated with POEMS; Toxin-Induced peripheral neuropathy; peripheral neuropathy associated with kidney disease; peripheral neuropathy associated with vasculitis; peripheral neuropathy associated with vitamin and nutrition deficiency; Charcot-Marie Tooth Disease (CMT); idiopathic peripheral neuropathy; fibromyalgia; and paraneoplastic peripheral neuropathy.

One embodiment of the invention is that the subject methods and plasma-comprising blood products and fractions can be used to treat wounds by promoting wound healing. Further embodiments of the invention include using the subject methods and plasma-comprising blood productions and fractions to treat chronic or acute wounds. Additional embodiments of the invention include treating: diabetic ulcers; pressure ulcers; venous ulcers; arterial ulcers; surgical wounds; traumatic wounds; and burns.

M. Reagents, Devices, and Kits

Also provided are reagents, devices, and kits thereof for practicing one or more of the above-described methods. The subject reagents, devices, and kits thereof may vary greatly.

Reagents and devices of interest include those mentioned above with respect to the methods of preparing plasma-comprising blood product for transfusion into a subject in need hereof, for example, anti-coagulants, cryopreservatives, buffers, isotonic solutions, etc.

Kits may also comprise blood collection bags, tubing, needles, centrifugation tubes, and the like. In yet other embodiments, kits as described herein include two or more containers of blood plasma product such as plasma protein fraction, such as three or more, four or more, five or more, including six or more containers of blood plasma product. In some instances, the number of distinct containers of blood plasma product in the kit may be 9 or more, 12 or more, 15 or more, 18 or more, 21 or more, 24 or more 30 or more, including 36 or more, e.g., 48 or more. Each container may have associated therewith identifying information which includes various data about the blood plasma product contained therein, which identifying information may include one or more of the age of the donor of the blood plasma product, processing details regarding the blood plasma product, e.g., whether the plasma product was processed to remove proteins above an average molecule weight (such as described above), blood type details, etc. In some instances, each container in the kit includes identifying information about the blood plasma contained therein, and the identifying information includes information about the donor age of the blood plasma product, e.g., the identifying information provides confirming age-related data of the blood plasma product donor (where such identifying information may be the age of the donor at the time of harvest). In some instances, each container of the kit contains a blood plasma product from a donor of substantially the same age, i.e., all of the containers include product from donors that are substantially the same, if not the same, age. By substantially the same age is meant that the various donors from which the blood plasma products of the kits are obtained differ in each, in some instances, by 5 years or less, such as 4 years or less, e.g., 3 years or less, including 2 years or less, such as 1 year or less, e.g., 9 months or less, 6 months or less, 3 months or less, including 1 month or less. The identifying information can be present on any convenient component of the container, such as a label, an RFID chip, etc. The identifying information may be human readable, computer readable, etc., as desired. The containers may have any convenient configuration. While the volume of the containers may vary, in some instances the volumes range from 10 ml to 5000 mL, such as 25 mL to 2500 mL, e.g., 50 ml to 1000 mL, including 100 mL to 500 mL. The containers may be rigid or flexible, and may be fabricated from any convenient material, e.g., polymeric materials, including medical grade plastic materials. In some instances, the containers have a bag or pouch configuration. In addition to the containers, such kits may further include administration devices, e.g., as described above. The components of such kits may be provided in any suitable packaging, e.g., a box or analogous structure, configured to hold the containers and other kit components.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

N. Experimental Examples

1. Models for Pain
    a) Pain—Treatment Before Injury
        (1) Alteration of Neuropathic Nerve Injury A chronic pain model employing chronic constrictive injury (CCI) was used to determine levels of pain experienced by 22-month-old C57BL/6J mice treated with: (1) PPF1 following CCI; (2) vehicle following CCI; or (3) vehicle following sham surgery. Using such a model, the nervous system becomes regulated to a persistent state of high reactivity which lowers the pain threshold long after the initial injury has occurred. (See, e.g., Safakhah, H. A. et. al., *Journal of Pain,* 10:1457-66 and Suter M R, et al., *Anesthesiology Res and Practice* (2011) which are herein incorporated by reference in their entirety).

PPF1 is a PPF with approximately 88% normal human albumin (in relation to total protein), 12% alpha and beta globulins, and no more than 1% gamma globulin as determined by electrophoresis. Except where noted, PPF1 is administered in the examples herein in vivo using a 5% solution (w/v, 50 g/L). PPF2 is also a PPF, but a different lot from PPF1. PPF2 meets the same protein content and concentration specifications as PPF1.

FIG. 1 depicts timeline of a CCI experiment. Twenty-three-month-old wild type mice were administered a CCI or sham surgery via ligation 24 hours prior to administration of a 7-consecutive-day pulse dosing regimen of 150 uL/day (intravenously tail-vein) of either PPF1 or vehicle control. Behavior was assessed during week four, and tissue collection for histology occurred at week five.

FIG. 2 is a representation depicting the location of the CCI administered to twenty-three-month-old wild type mice. The ligation was administered on the sciatic nerve as indicated by the figure. The figure was adapted from Suter M R, et al., *Anesthesiology Res and Practice*, (2011), which is incorporated herein by reference in its entirety.

FIG. 3 reports data from a mechanical von Frey allodynia test in wild-type mice 4 weeks after CCI or sham surgery as detailed in FIG. 1. To determine an animal's tolerance to mechanical pressure, the hind paw enervated by the subject sciatic nerve, was stimulated by differing thicknesses of von Frey filaments. The pressure at which the mouse withdrew its hind paw was measured and plotted in FIG. 3. The figure illustrates that mice treated with PPF1 after CCI exhibited significantly less pain (could withstand more pressure) than those treated with vehicle control after CCI. Sham surgery animals also exhibited significantly less pain that those treated with vehicle control after CCI. The primary finding is that PPF1 has a positive effect on mechanical nociception deficits induced by CCI. *** $P<0.001$ CCI treated with PPF1 vs. CCI Vehicle treatment, *$P<0.05$ Sham vehicle vs. CCI vehicle; One-way ANOVA with Tukey post-hoc analysis.

FIG. 4 reports data from hippocampal histology performed on the wild type mice described in FIG. 1. Neurogenesis was measured using the doublecortin (DCX) marker. Mice who received CCI surgery and were treated with PPF1 had significantly increased neurogenesis in the dentate gyrus of the hippocampus than those who received vehicle. Mice who received sham operation trended towards greater neurogenesis than mice who received CCI surgery, both groups received vehicle treatment post-surgery. Thus, PPF1 exhibited the ability to restore neurogenesis after chronic nerve injury. *$P<0.05$ CCI treated with PPF1 vs. CCI Vehicle treatment; Unpaired T-Test.

FIG. 5 reports data from hippocampal histology performed on the wild type mice described in FIG. 1 Inflammatory marker as measured by CD68 expression was quantified. Our findings illustrate that mice which received CCI surgery and vehicle treatment expressed a significantly greater number of CD68 positive cells in the hippocampus than those were treated with PPF1 following CCI surgery. PPF1 treated animals had similar inflammation levels to that of the sham surgery group. This illustrates that PPF1 can help to ameliorate neuroinflammation resulting from chronic nerve injury. *$P<0.05$ CCI treated with PPF1 vs. CCI Vehicle treatment, Sham vehicle vs. CCI vehicle; One-way ANOVA with Tukey post-hoc analysis.

FIG. 6 reports data from a mechanical von Frey allodynia test in C57BL/6J mice which received CCI or sham surgery and tested in a timeline as described in FIG. 1. Twenty-two-month-old mice were administered a 7-consecutive-day pulse dosing regimen of 150 uL/day (intravenous tail-vein) of either PPF1 or vehicle control. Another group received Gabapentin at 75 mg/kg (intraperitoneal administration) daily for 7 consecutive days. All treatments were initiated 24 hours after CCI or sham surgery. To determine an animal's tolerance to mechanical pressure, the hind paw enervated by the subject sciatic nerve, was stimulated by differing thicknesses of von Frey filaments. The pressure at which the mouse withdrew its hind paw was assessed and represented in FIG. 6 as weeks post CCI or sham surgery. The figure illustrates that mice administered PPF1 following CCI surgery had significantly increased tolerance to mechanical nociception at all assessed timepoints than those treated with vehicle after CCI. Conversely, mice administered Gabapentin only show significant improvement in mechanical nociception at 2 weeks following CCI surgery and are similar to vehicle treated mice at all other timepoints. Sham surgery mice show significantly increased response to mechanical nociception at 3 and 5 weeks following surgical manipulation. Together, these data illustrate that PPF1 ameliorates peripheral pain for a greater amount of time than that of standard of care treatments (Gabapentin). *, ** P<0.001, P<0.0001 PPF1 vs. Vehicle control; ANOVA with Tukey Post-hoc analysis. * P<0.05 Gabapentin vs. Vehicle control; ANOVA with Tukey Post-hoc analysis. *, ** P<0.05, P<0.01 Sham vs. Vehicle control; ANOVA with Tukey Post-hoc analysis.

FIG. 7 reports data from a hot plate test on wild-type mice treated as described in FIG. 1 and as described by Woolfe and Macdonald. (Woolfe G. and Macdonald A D, *J. Pharmacol. Exp. Ther.* 80:300-07 (1944), which is incorporated by reference herein in its entirety). The hot plate is set to a temperature of 55° C. Mice are acclimated to being placed inside a clear cylinder for 30 minutes. The cylinder is placed upon the hot plate and a timer started. When nocifensive behaviors (e.g. hind paw licking or jumping) are first observed, the time is recorded as latency. If no nocifensive behaviors are observed, the animal is removed at a predetermined cut-off time such as 30 seconds to prevent tissue damage. Mice are only tested at 2- and 5-weeks post CCI surgery, as repetitive exposure to testing has been shown to alter sensitivity. FIG. 7 illustrates hot plate nocifensive latency 5 weeks after CCI or sham surgery. PPF1 treatment are significantly less sensitive to hot plate stimuli compared to mice given CCI plus vehicle control, indicating a rescue effect by PPF1.  P<0.01 Sham vs. CCI surgery, ** P<0.0001 PPF1 vs. Vehicle treated CCI surgery mice. ANOVA with Tukey Post-hoc analysis.

(2) Prevention of Neuroinflammation in the Spinal Cord

A separate study similar to the preceding study (above) was performed on 22-month-old C57BL/6J mice. Cohorts of mice were treated as follows: (1) PPF (PPF2) following CCI; (2) vehicle following CCI; (3) recombinant human albumin (rhAlb) following CCI; or (4) vehicle following sham surgery. Mice were administered a 7-consecutive-day pulse dosing regimen of 150 μL/day (intravenous tail-vein) of PPF2, recombinant human albumin, or vehicle control. All treatments were initiated 24 hours after CCI or sham surgery.

FIG. 8 reports data from a hot plate test (as described above) thirty-five (35) days post CCI as treated in the timeline of FIG. 1. PPF2-treated mice were significantly less sensitive to hot plate stimuli compared to mice given CCI plus vehicle control. Mice treated with recombinant human albumin were also significantly less sensitive to mice given CCI plus vehicle control, but not to the degree of mice treated with PPF2. * P<0.05 rhAlb vs. vehicle treated CCI mice, *** P<0.001 PPF2 vs. vehicle treated CCI surgery mice. ANOVA with Tukey Post-hoc analysis.

FIG. 9 reports data from a mechanical von Frey allodynia test in these same mice at different time intervals both pre- (baseline) and post-CCI. The pressure at which the mouse withdrew their hind paws was assessed and is represented in FIG. 9 as weeks post CCI or sham surgery. The figure illustrates the mice administered PPF2 following CCI surgery had significantly increased tolerance to mechanical nociception at all assessed timepoints than those treated with vehicle or recombinant human albumin (rhAlb) after CCI. This shows that a PPF (PPF2) ameliorated pain for a greater amount of time than control vehicle or albumin, albumin being the major protein component of PPF. Thus, these effects appear not to be mediated via albumin, but to other proteins present in PPF. * P<0.05;  P<0.01; * P<0.001; **** P<0.0001 vs. vehicle control; ANOVA with Tukey Post-hoc analysis.

FIG. 10 reports the relative levels of myelin basic protein (MBP, detected by Abcam, ab40390 anti-rabbit antibody) in the distal sciatic nerve five weeks after the last dose of PPF (PPF1) in another similar experiment conducted in 22-month-old mice as described above. * P<0.05; *** P<0.001 vs. vehicle control; ANOVA with Tukey Post-hoc analysis.

FIG. 11 reports the relative levels in these mice of S-100 Schwann cell marker. In both cases, PPF in mice with CCI increased relative levels of these markers compared to vehicle control mice with CCI. Together this shows that PPF promotes sciatic nerve repair mechanisms via increasing myelin protein and S-100 protein expression. It also shows that PPF induces myelination repair mechanisms.  P<0.01; * P<0.001 vs. vehicle control; ANOVA with Tukey Post-hoc analysis.

FIG. 12 is a fluorescence microscopic qualitative representation of the data reported in FIGS. 10 and 11.

FIG. 13 and FIG. 14 show detection of BDNF and CD68, respectively, in the dorsal horn of the spinal cord in mice treated 24 hours post-CCI injury. Brain-derived neurotrophic factor (BDNF, detected by Abcam, ab108319 anti-rabbit antibody) is secreted by activated microglia and it has been shown to enhance spinal nociception (detection of painful stimuli) through synaptic facilitation and engagement of central sensitization-like mechanisms. Peripheral injury-induced neuropathic pain is often accompanied with increased spinal expression of BDNF (Garraway S M, et al. *Neural Plast.* Article ID 9857201 (2016)). CD68 levels (detected by Biorad MCA1957 GA anti-rat antibody) were also determined. CD68 is a marker for activated microglia. FIGS. 13 and 14 show that PPF treatment 24 hours after CCI injury results in significant reduction of both BDNF and CD68 markers in the dorsal horns of the spinal cord, indicating the prevention of microglial activation and blocking of deleterious downstream events linked to development of neuropathic pain.  P<0.01; * P<0.001 vs. vehicle control; ANOVA with Tukey Post-hoc analysis.

FIGS. 15 and 16 are fluorescent microscopic images of the data presented in FIGS. 13 and 14, respectively. The rectangle highlights the dorsal horns of the spinal cord which was analyzed at the L4-L6 lumbar spinal segments. The images on the right sides of the figures are higher focal powered images of the rectangular regions on the left sides of each figure.

b) Pain—Treatment Fourteen Days After Injury

FIG. 17 shows the protocol used on 22-month-old C57BL/6J mice. Baseline von Frey paw withdrawal thresholds for measuring mechanical allodynia were taken 3-4 days before CCI or sham procedures. Cohorts of mice were treated as follows: (1) PPF (PPF1) 14 days following CCI; (2) vehicle 14 days following CCI; (3) recombinant human albumin (rhAlb) 14 days following CCI; or (4) vehicle 14 days following sham surgery. Mice were administered a 7-consecutive-day pulse dosing regimen of 150 μL/day (intravenous tail-vein) of PPF1, recombinant human albumin, or vehicle control. All treatments were initiated 14 days after CCI or sham surgery.

FIG. 18 reports the Von Frey paw withdrawal thresholds at baseline, 14, 21, 28, 35, 42, and 49 days post-CCI. At Day 14, a significant deficit is seen in all but the sham group, indicating that there is central sensitization in all CCI groups after 2 weeks of injury. This is not reversed until 7 days after cessation of treatment with PPF (Day 28), indicating that simple analgesia does not take place with PPF in this model. Instead, a mechanistic effect takes place with PPF treatment which is not observed with vehicle or recombinant human albumin (rh Albumin). This shows that pain that is fully established before PPF treatment (which necessarily involves a central component) is significantly alleviated by PPF compared to vehicle control.  $P<0.01$; * $P<0.001$; **** $P<0.0001$ vs. vehicle control; ANOVA with Tukey Post-hoc analysis.

FIGS. 19 and 20 report the hot plate latency values at 35 Days post-CCI (FIG. 19) and 49 Days post-CCI (FIG. 20). Both sets of results show that the PPF-treated mice had long-lasting reductions of hot plate pain sensitivity. This also supports the observation that PPF works through a mechanistic effect as opposed to simply providing an analgesic effect. ** $P<0.01$; ANOVA with Tukey Post-hoc analysis.

2. Model for Wound Healing

A mouse model of diabetes (B6. BKS(D)-Lepr$^{db}$/J) was used to assess the efficacy of PPF1 on wound healing. Six-week-old male B6. BKS(D)-Leprdb/J mice were shaved on their back on day −1. Mice were wounded on Day 0 on two locations on their back. Mice received daily treatments (IV) of vehicle (150 μL) or PPF1 (150 μL) from day 0 (immediately after skin wounding) to 6 included.

Skin wounding was performed as follows: Animals were depilated the day before skin wounding using a depilating cream followed by gentle wash of their skin with warm water. Animals were anesthetized using inhalant isoflurane, surgical site was shaved and prepped with povidone-iodine ("betadine") or chlorhexidine antiseptic products (or similar surgical scrub) and 70% ethanol. Hot water heat pad (or similar surgical product) was placed underneath the mice. Two wounding sites were marked on their dorsal skin with 5 mm-diameter circles using a permanent marker. The dorsal skin was lifted using clean forceps and cut using fine surgical scissors alongside the marked circles. A 15 mm-diameter silicone splint with a 6 mm-diameter cut in its middle was applied around the wound using Vetbond and nylon suture thread. After skin wounding, mice were weighed (initial body weight) and placed in a clean home cage with a heating pad underneath and softened food. Mice stayed on pad and were monitored, until mice were Bright, Alert, and Reactive.

Postoperatively, wound healing was assessed daily until sutures were removed. Buprenorphine was administered i.p. right after surgery and every ~12 hours for a total of three injections. Meloxicam was administered i.p. prior to surgery and 24 hours post-surgery. Softened food and Clear $H_2O$ Recovery gel will be placed on the bottom of the cage after surgery. Mouse body weight was measured daily post-surgery. If a mouse lost more than 1 gram body weight since post-surgery weight, 500 ul saline/day was administered.

Mice were evaluated daily for their amount of wound closure by measuring the wound size using a caliper. Mice were sacrificed on Days 10 and 14. Mice were deeply anesthetized with Avertin (250 mg/kg IP) and then subjected to cardiac puncture and blood samples collected with pre-filled syringes with EDTA. Blood/EDTA was then injected into a microcentrifuge tube. The tubes were kept on ice and plasma separated by centrifugation at 1000 g (+4° C.) for 15 min as soon as was possible. Plasma from each mouse is aliquoted at 100 μL per vial, with the remainder in a second vial, and stored at −80° C.

Skin was collected from each mouse, fixed and 4% paraformaldehyde followed by 2 washes in PBS and subsequently paraffin embedded. Tissues are sectioned or lysed and analyzed for markers of inflammation by standard histological and biochemical methods, including qRT-PCR, Western blot, ELISA, and immunohistochemistry.

FIG. 21 is a histological comparison between a diabetic wound (B6.BKS(D)-Lepr$^{db}$/J diabetic mouse model) that was untreated (FIG. 21A) or with PPF1 (FIG. 21B). Black bars indicate wound bed thickness (epidermal plus granulation layer). Arrows indicate wound boundaries. Wound bed thickness was increased in PPF1-treated mice as determined by wound bed thickness. PPF1 therefore demonstrates improved wound healing.

FIG. 22 is a histological comparison between a diabetic wound (B6. BKS(D)-Lepr$^{db}$/J diabetic mouse model) that was untreated (FIG. 22A) or with PPF1 (FIG. 22B). Black bars indicate the granulation layer. Blue bars indicate the epidermal layer. The PPF1-treated wound exhibited a thicker epidermal layer than the untreated wound, however the granulation layer exhibited an even greater trend in the difference between PPF1-treated and untreated wounds (i.e. the granulation layer was thicker in the PPF1-treated wounds than the untreated wounds).

FIG. 23 through FIG. 26 report results from the B6 ob/ob (B6. Cg-Lepob/J mice) diabetic mouse model assessing the efficacy of PPF1 versus vehicle on diabetic wound healing. Nine-week-old male B6 OB/OB mice were used. The day before wounding, mice were weighed and fasted for 5 hours to determine fasting glucose from tail blood. The mice were equally divided into 2 different treatment groups according to weight and glucose level. For wounding, mice were shaved, applied with hair removal cream (Nair™), wounded on two locations on their back (5 mm diameter excision), then applied with a silicone ring soaked in 70% alcohol (12 mm outer circumference and 6 mm inner circumference). The ring was attached to the open wound with Vectabond™. Four sutures were applied to each ring to ensure that the silicone ring stayed attached to the wound through the entire course of the experiment. 30 μL of PPF1 and control were applied directly on top of the wound and the two wounds sealed with a piece of Tegaderm™. Daily treatments were administered by injecting PPF1 and control inside the Tegaderm™ that covered the wounds. To image the wounds, the Tegaderm™ that was just covering the wound was cut off and the wound resealed with a fresh piece of Tegaderm™. At sacrifice, the rings were removed, and the wounds were cut from the back for histology.

Wound healing was assessed daily by determining the amount of wound closure. Wound size was measured using a camera and a precision ruler for scale. Terminal tissue collection was performed on Days 10 and 14. Tissues were sectioned or lysed and analyzed for markers of inflammation by standard histological methods including immunohistochemistry, qRT-PCR, and H&E and other special stains.

FIG. 23 depicts the general design of the experiment. Blood drops indicate when blood was collected to measure fasting glucose level. On Day 2, the skin wound was made, and on Days 1-7 intravenous (iv) dosing was performed. FIG. 24 reports the percentage of the wound still open at several time points post-wounding in a first study (Study 1). Mice were treated with either PPF1 (150 μL) for 7 days or saline control. After 10 days, the sizes of the open wounds in PPF1-treated animals was significantly reduced compared to saline control. (** $p<0.006$ by unpaired T-test).

FIG. 25 reports the percentage of the wound still open at several time points post-wounding in a second similar study (Study 2). Mice were treated with either PPF1 (150 μL) for 7 days or saline control. After 8 days, the sizes of the open wounds in PPF1-treated animals was significantly reduced compared to saline control. (** $p<0.0018$ unpaired T-test).

FIG. 26 reports the percentage of the wound still open at 11 days post-wounding, combining the data from Studies 1 and 2. PPF1-treated animals exhibits a statistically-significant decrease in the percentage of wound left open after 11 days. ( $p<0.006$ by unpaired T-test). The difference between PPF1-treated and vehicle-treated animals at Day 10 was similarly significant ( $p<0.006$ by unpaired T-test).

FIG. 27 and FIG. 28 report the results of a study using topically-administered PPF1 or vehicle to wounds in B6 ob/ob (B6. Cg-Lepob/J mice). FIG. 27 shows the study paradigm of daily administrations of 30 μL of topical PPF1 or control vehicle administered to the wounds. Wounding was performed as described in FIG. 23. FIG. 28 reports the results of the topical study, with percentage of the area of the initial wound left after 10 days of treatment. FIG. 28 indicates that PPF1 significantly decreased percentage of the open wound left after 10 days compared to control vehicle.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of treating a subject for peripheral neuropathy, the method comprising administering an effective amount of a Plasma Fraction to the subject.

2. The method of claim 1 wherein the Plasma Fraction is a Plasma Protein Fraction.

3. The method of claim 2 wherein the Plasma Protein Fraction comprises between 83% to 95% albumin.

4. The method of claim 3 wherein the Plasma Protein Fraction is a commercially available Plasma Protein Fraction.

5. The method of claim 1 wherein the Plasma Fraction is a HAS.

6. The method of claim 5 wherein the HAS is commercially available HAS.

7. The method of claim 1 wherein the administering is performed using a Pulse Dose dosing regimen.

8. The method of claim 1 wherein the peripheral neuropathy comprises peripheral neuropathy associated with post-operative recovery.

9. The method according to claim 1 wherein the peripheral neuropathy is associated with carpal tunnel syndrome.

10. The method according to claim 1 wherein the peripheral neuropathy comprises chemotherapy-induced peripheral neuropathy.

11. The method according to claim 1 wherein the peripheral neuropathy is associated with compression and trauma.

12. The method according to claim 1 wherein the peripheral neuropathy comprises diabetic neuropathy.

13. The method according to claim 1 wherein the peripheral neuropathy is associated with shingles.

14. A method of treating a subject for chemotherapy-induced peripheral neuropathy, the method comprising administering an effective amount of a Plasma Fraction to the subject.

15. The method of claim 14 wherein the Plasma Fraction is a Plasma Protein Fraction.

16. The method of claim 15 wherein the Plasma Protein Fraction comprises between 83% to 95% albumin.

17. The method of claim 16 wherein the Plasma Protein Fraction is a commercially available Plasma Protein Fraction.

18. The method of claim 14 wherein the Plasma Fraction is a HAS.

19. The method of claim 18 wherein the HAS is commercially available HAS.

20. The method of claim 14 wherein the administering is performed using a Pulse Dose dosing regimen.

* * * * *